United States Patent [19]

Rakhimov et al.

[11] Patent Number: 5,707,911
[45] Date of Patent: Jan. 13, 1998

[54] INFRARED RADIATION GENERATING CERAMIC COMPOSITIONS

[75] Inventors: Roustam Khakimovich Rakhimov; Elena Vasilievna Kim, both of Tashkent, Uzebkistan

[73] Assignee: Mitech Scientific Corp., Flanders, N.J.

[21] Appl. No.: 479,420

[22] Filed: Jun. 6, 1995

Related U.S. Application Data

[60] Division of Ser. No. 962,372, Oct. 16, 1992, Pat. No. 5,472,720, which is a continuation-in-part of Ser. No. 900,228, Jun. 17, 1992, Pat. No. 5,350,927.

[51] Int. Cl.[6] .................................................. C04B 35/185
[52] U.S. Cl. .......................... 501/128; 501/132; 501/126; 501/133; 501/118; 501/119; 501/121; 501/122; 501/125; 501/154
[58] Field of Search ........................... 252/587; 501/132, 501/120, 102, 123, 126, 128, 127, 153, 154, 104, 117, 904, 152, 133, 118, 121, 122, 125

[56] References Cited

U.S. PATENT DOCUMENTS

| | | | |
|---|---|---|---|
| H302 | 7/1987 | Nevitt et al. | 501/103 |
| Re. 32,449 | 6/1987 | Claussen et al. | 501/103 |
| 3,284,217 | 11/1966 | Walther | 106/59 |
| 3,475,352 | 10/1969 | Barbier et al. | 252/520 |
| 3,574,142 | 4/1971 | Yerouchalmi et al. | 252/520 |
| 3,585,390 | 6/1971 | Ishikawa | 219/553 |
| 3,625,717 | 12/1971 | Grubba et al. | 106/39 R |
| 3,730,911 | 5/1973 | Aubin et al. | 252/516 |
| 4,000,983 | 1/1977 | Alexandrov et al. | 29/182.5 |
| 4,013,592 | 3/1977 | Matsuoka et al. | 501/132 |
| 4,045,375 | 8/1977 | Komatu | 252/319 |
| 4,101,454 | 7/1978 | Kulwick et al. | 252/514 |
| 4,110,260 | 8/1978 | Yamamoto et al. | 252/519 |
| 4,141,743 | 2/1979 | Grubba | 106/66 |
| 4,330,630 | 5/1982 | Jeanviore et al. | 501/105 |
| 4,551,616 | 11/1985 | Buttery | 219/553 |
| 4,551,617 | 11/1985 | Crossley et al. | 219/464 |
| 4,568,848 | 2/1986 | Ogawa | 310/313 |
| 4,774,415 | 9/1988 | Biegel et al. | 250/455.1 |
| 4,776,895 | 10/1988 | Goldstein | 136/253 |
| 4,855,265 | 8/1989 | Day et al. | 501/128 |
| 4,864,104 | 9/1989 | Crossley et al. | 219/464 |
| 4,902,876 | 2/1990 | Mewissen | 219/464 |
| 5,006,489 | 4/1991 | Nagel et al. | 501/15 |
| 5,057,478 | 10/1991 | Abe et al. | 502/159 |
| 5,104,830 | 4/1992 | Droyet et al. | 501/9 |
| 5,130,281 | 7/1992 | Sano et al. | 501/138 |
| 5,195,165 | 3/1993 | Ono et al. | 219/553 |

FOREIGN PATENT DOCUMENTS

| | | | |
|---|---|---|---|
| 74-009494 | 3/1974 | Japan. | |
| 49-088916 | 8/1974 | Japan. | |
| 1-227376 | 9/1989 | Japan. | |
| 2-110137 | 4/1990 | Japan. | |
| 4-131013 | 5/1992 | Japan. | |
| 1172904 | 8/1985 | U.S.S.R. | 501/117 |
| 811987 | 4/1959 | United Kingdom | 501/117 |
| 1527955 | 10/1978 | United Kingdom. | |

OTHER PUBLICATIONS

G.A. Slack, "Advanced Materials for Optical Windows" GE Res. Rept. 79CRD071, Jun., 1979.

*Primary Examiner*—Melissa Bonner
*Attorney, Agent, or Firm*—John A. Parrish

[57] ABSTRACT

The disclosed invention is directed to novel ceramic compositions, and to stabilizer compositions for use with those ceramic compositions. The ceramic materials are formed of rare earth chromium oxides that include a novel combination of stabilizing compounds. Also, dryer or sterilizer devices which incorporate these ceramic compositions for generating infrared radiation for drying or sterilizing various articles.

2 Claims, 9 Drawing Sheets

INFRARED RADIATION GENERATING CERAMIC COMPOSITIONS

This is a division of application Ser. No. 07/962,372, filed Oct. 16, 1992, now U.S. Pat. No. 5,472,720, which is a continuation-in-part of application Ser. No. 07/900,228, filed Jun. 17, 1992, which issued Sep. 27, 1994 as U.S. Pat. No. 5,350,927.

FIELD OF THE INVENTION

The invention generally relates to ceramic materials and their methods of manufacture. The invention particularly relates to refractory ceramic materials of improved thermal, chemical and physical stability and resistance to thermal cycling. The invention also relates to the use of the presently disclosed ceramic compositions in devices for drying or for fast and effective sterilization of various articles.

BACKGROUND

Ceramic materials of the formula $RCrO_3$, where R is a rare earth oxide as yttrium oxide are known in the art. See, e.g., U.S. Pat. No. 3,475,352. These materials, although useful in electroconductive applications such as electrodes, suffer from low chemical stability when exposed to high temperatures above 1600° C., low resistance to thermal cycling at temperatures above 1500° C., and the inability to be heated at high heating rates. These deficiencies have limited the use of these materials in applications where property stability is important.

A need therefore exists for rare earth oxide ceramic materials that have improved stability and which are useful in electroconductive applications as well as in high temperature environments. Such applications include the drying or sterilization of various articles.

One known method of sterilization uses infrared radiation (IR). For example, U.S. Pat. No. 4,774,415 discloses a device for sterilizing a hose coupling from a dialysis apparatus. One drawback of this device is that the source can cause insufficient sterilization of portions of the articles which do not receive the appropriate exposure of IR. If the time of sterilization is increased to compensate for the inadequate exposure, portions of the articles to be sterilized can be overheated. When articles made of metals and glass are overexposed, they can either be melted due to overheating or discolored due to oxide film formation.

Automatic regulation of the temperature by using a temperature detector and electronics for control and operation does not improve this problem because the articles often have different sizes and masses which are in conflict or incompatible with the constant and inflexible size and mass of the temperature detector. Thus, the present invention proposes to eliminate the above drawbacks and to increase the efficiency of sterilization by decreasing the sterilization time through the use of such new ceramic materials.

The drying of food products using IR produced by the use of a transforming member or screen made of mullite is known from an article by G. A. Slack entitled "Advanced Materials for Optical Windows" GE Res. Rept. No. 79CRD071, June, 1979. The primary deficiency of this method is its low drying efficiency. Thus, the present invention also proposes to increase the efficiency of IR drying methods, again through the proper selection and use of the new ceramic materials disclosed herein.

SUMMARY OF THE INVENTION

The present invention is directed to novel ceramic compositions having improved thermal, chemical and physical properties. These materials are useful in a variety of applications where rapid heating rates and property stability are important. For example, the ceramic materials of the invention may be used to generate infrared radiation of certain wavelengths.

In accordance with the invention, a ceramic composition having surprisingly stable thermal, chemical and physical properties is provided. The ceramic composition is formed of a rare earth chromium oxide and a novel composition of additives that includes alkaline earth spinels such as alkaline earth aluminate spinels, alkaline earth chromates, and, optionally, alkaline earth zirconates or alkaline earth hafniates for stabilizing the rare earth chromium oxide. The alkaline earth spinels preferably are any one of $MgAl_2O_4$, $SiO:Al_2O_3$, or $CaO:Al_2O_3$ and most preferably $MgAl_2O_4$. The alkaline earth zirconate may be $CaZrO_3$, and the alkaline earth hafniate may be $CaHfO_3$. Preferably, the stabilizing composition amounts to about 5 to 35 percent by weight, most preferably 5 to 15 percent by weight, of the ceramic composition.

The alkaline or rare earth chromate used in the composition may be magnesium chromate, yttrium chromate, scandium chromate, terbium chromate, or ytterbium chromate, and most preferably, magnesium chromate. The rare earth chromium oxide ceramic compositions of the invention may also include at least one of an oxide of zirconium or hafnium in an amount of about 0.5 to 5 weight percent, a chromate of yttrium, scanadium, ytterbium, or terbium in an amount of about 0.5 to 5 weight percent, or an oxide of cerium, dysprosium, lutetium, or europium in an amount of about 0.1 to 1 weight percent. The rare earth chromium oxide can be lanthanum chromate, neodymium chromate, samarium chromate or mixtures thereof, and most preferably is lanthanum chromate.

As mentioned, a stabilizer composition for imparting improved thermal, chemical and physical properties is included in the ceramic compositions of the invention. The stabilizer composition includes sufficient amounts of an alkaline earth spinel and an alkaline earth chromate which, in combination, stabilize the thermal, chemical and physical properties of the ceramic composition. Preferably, the alkaline earth spinel is $MgAl_2O_4$, and the alkaline earth chromate is $CaCrO_4$, $MgCrO_4$, or $SrCrO_4$. The stabilizer may further include an alkaline earth zirconate or alkaline earth hafniate such as $CaZrO_3$ or $CaHfO_3$.

The invention further is directed to silica containing compositions that also have surprisingly stable thermal, chemical and physical properties. These compositions can include $SiO_2$ in an amount of 10 to 28 weight percent and $Fe_2O_3$ in an amount of 15 to 35 weight percent, with the balance being $Cr_2O_3$. One or more of the following compounds in the following amounts may be included in these silica containing compositions: $Al_2O_3$ in an amount of about 0.5 to 3.5 weight percent, CuO in an amount of about 0.1 to 2 weight percent, CaO in an amount of about 0.5 to 15 weight percent, and MgO in an amount of about 0.1 to 3 weight percent. In these silica compositions, each of $Al_2O_3$, CuO, CaO and MgO can be present as an additive in the amount stated. Advantageously, at least two and as many as four of these additives may be present in the aforementioned amounts.

Another aspect of the present invention relates to an apparatus for drying or sterilizing articles comprising a chamber for receiving articles to be dried or sterilized; means for providing energy within the chamber; and a first ceramic material associated with the chamber for receiving and absorbing energy from the providing means and for emitting infrared radiation of one or more selective wavelengths which radiation is directed toward the articles for drying or sterilization thereof.

In this apparatus, the providing means includes an energizable article which is operatively associated with the first ceramic material such that a substantial portion of the energy generated by the article is received and absorbed by the first ceramic material. When the first ceramic material is positioned adjacent at least a portion of the energizable article, a significant portion of the energy generated by the providing means is received and absorbed by the first ceramic material. Preferably, the providing means comprises a plurality of energizable articles each having an energy emitting surface, and the first ceramic material is positioned adjacent a portion of the energy emitting surface of each article within the chamber. The first ceramic material may form a concentric tube around at least one of the articles, and, if desired, around each article, and the apparatus may include means for supporting the articles to be dried or sterilized.

For optimum operation, the apparatus further comprises a second ceramic material associated with the chamber for emitting infrared radiation of one or more wavelengths, which radiation is the same as or different from that emitted by the first ceramic material. This radiation is directed toward the articles for drying or sterilization thereof. This second ceramic material is associated with the chamber for receiving and absorbing infrared radiation from the first ceramic material, and is positioned adjacent at least a portion of the first ceramic material such that a significant portion of the infrared radiation emitted by the first ceramic material is received and absorbed by the second ceramic material. The second ceramic material should be positioned adjacent a substantial portion of the first ceramic material, such as in the form of a concentric tube around the first ceramic material. The second ceramic material may also be configured in the form of a plate which is positioned near the energizable elements to receive substantially all infrared radiation emitted from the first ceramic material.

Preferably, the energizable article comprises a halogen lamp or a high resistance wire coil within a glass tube, while first ceramic material comprises the rare earth chromium oxide ceramic composition described above, and the second ceramic material comprises the chromic oxide composition described above.

The invention is further directed to methods for treating a material with infra-red radiation to preserve at least one property of the material. Typically, a ceramic composition having chromium oxide or rare earth chromium oxide is heated to a temperature sufficient to generate infra-red radiation, and the radiation is directed to the material for a time sufficient to preserve at least one property of the material. The ceramic composition can be at least one of formulations A, B, C, D, E, or F as described below. A wide range of materials can be treated including foodstuffs such as potatoes, carrots, onions, and fruits; plastics such as amides, plant seeds such as cotton seeds, tomato seeds, and pepper seeds; silkworm pupae and cocoons, biologically active compounds such as phospholipase D, phospholipase D+, phospholipase A2, trypsin, and phenoloxidase; and wine.

In treating silkworm pupae and cocoons, formulation C heated to about 180–200 C. can be employed. Similarly, formulation A heated to 200–800 C. is useful for treating foodstuffs; formulations B or C heated to 300 C. for treating plastics; formulation A heated to 300–800 C. for treating plant seeds; and formulations C and B heated to 100–300 C. for treating wine and biologically active compounds.

Infra-red radiation generated by the method of the invention also advantageously can be employed to rapidly bake and cook foodstuffs such as bread dough, potatoes, and beef while preserving flavor by use of ceramic composition of formulation C to a temperature of about 600° C. to 800° C.

BRIEF DESCRIPTION OF THE DRAWINGS

Preferred embodiments of the dryer and sterilizer apparatus of the invention are illustrated in the attached drawing figures, wherein.

DETAILED DESCRIPTION OF THE INVENTION

Figure 1:
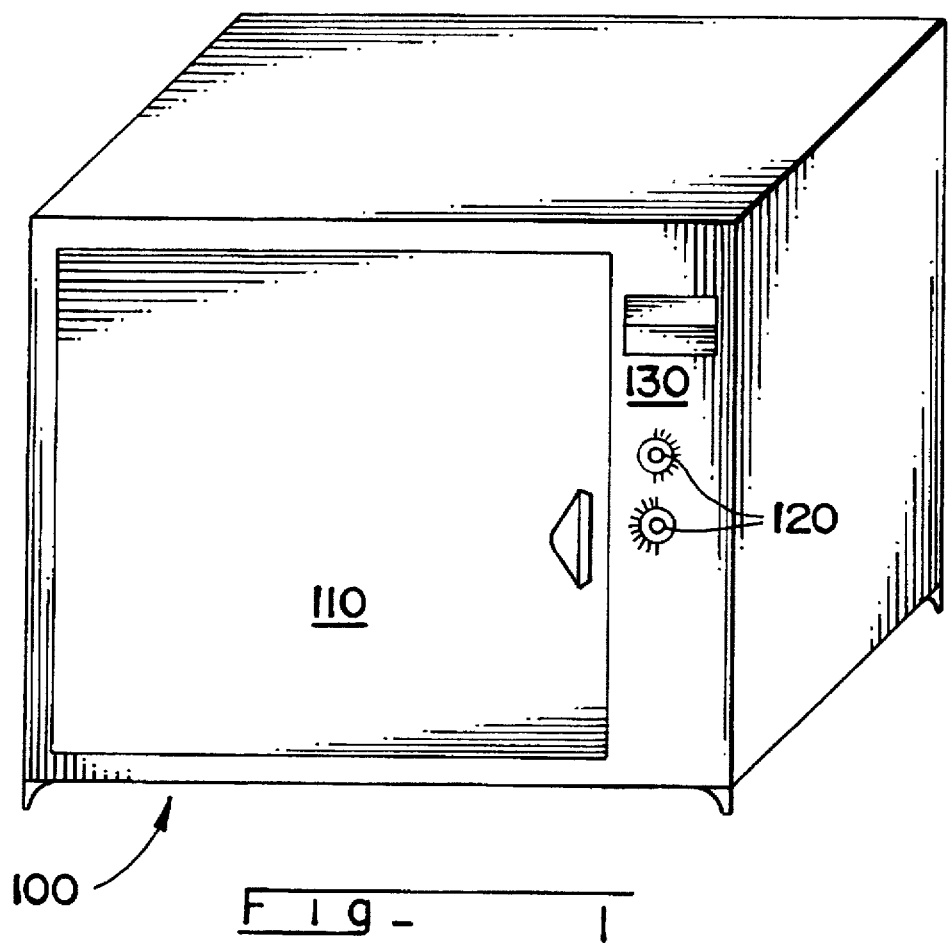
FIG. 1 is a perspective view of a sterilizer or dryer device in accordance with the invention.

Generally, the improved ceramic materials of the invention are formed from a mixture of rare earth chromium oxides and a novel combination of stabilizing compounds of an alkaline earth aluminate spinel such as $MgAl_2O_4$, an alkaline earth chromate such as $MgCrO_4$, and optional amounts of an alkaline earth zirconate such as $CaZrO_3$. This unique combination of additives enables the rare earth chromium oxide ceramic compositions of the invention to possess surprisingly increased thermal, chemical and physical properties. This unique combination of stabilizing compounds, moreover, enables the rare earth chromium oxide compounds to be heated at surprisingly high heating rates.

In accordance with the invention, electroconductive ceramic compositions formed of a mixture of rare earth chromium oxides of the formula $RCrO_3$ and a novel combination of stabilizing compounds is provided. In the formula $RCrO_3$, R is any one of lanthanum, neodymium, and samarium, preferably lanthanum or neodymium, and most preferably lanthanum.

The combination of stabilizing compounds includes alkaline earth spinels such as $MgAl_2O_4$, $SrO:Al_2O_3$, or CaO:Al₂O₃, and most preferably MgAl₂O₄, an optional amount of alkaline earth zirconate or alkaline earth hafniate, preferably CaZrO₃ or CaHfO₃, and an alkaline earth chromate such as MgCrO₄, SrCrO₄, or CaCrO₄, and most preferably MgCrO₄. This combination of additives may be present in an amount of about 1–35 weight percent, and most preferably about 1.5–26 weight percent of the overall rare earth chromium oxide ceramic composition. The rare earth chromium oxide ceramic materials of the invention are illustrated by the general composition below:

FORMULATION A

| Component | Weight Percent |
|---|---|
| MgAl₂O₄ | 0.5–10 |
| MgCrO₄ | 1.0–15 |
| CaZrO₃ | up to 10 |
| YCrO₃ | up to 5 |
| ZrO₂ | up to 5 |
| CeO₂ | up to 1 |
| LaCrO₃ | remainder |

Typically, the preparation of the chromium oxide and silica ceramic compositions of the invention is accomplished by ball milling components such as rare earth chromium oxides and stabilizer compounds in a plastic lined planet mill with Teflon balls to provide a finely ground powder. The powder is melted, ground, dried and pressed into shaped articles. The shaped articles then are sintered to provide a final product. Melting of these materials generally is accomplished under conditions which minimize the loss of oxygen from the formulated powder. Typically, the rare earth chromium oxide ceramic compositions can be melted at temperatures of about 2500° C. The silica based ceramic compositions typically can be melted at about 1900° C. Preferably, melting is accomplished in oxidizing atmospheres, most preferably air.

Sintering of the rare earth chromium oxide compositions is performed in oxidizing atmospheres at temperatures up to about 1700° C., preferably at about 1600° C. for about 12 hours. Sintering of the silica based compositions is also performed in oxidizing atmospheres at temperatures up to about 1800° C., preferably at about 1500° C. for 12 hours. Furnaces suitable for sintering at these temperatures in oxidizing atmospheres are illustrated by furnaces that employ LaCrO₃ heating elements. After sintering, the resultant articles are heated to high temperatures for extended time periods in oxidizing atmospheres such as at about 1500° C. to evaluate thermal, physical and mechanical properties such as compressive strength. Samples also are heated for about 20 hours at about 1600° C. to evaluate weight loss. Additional samples are metallized to evaluate specific resistance.

Samples are evaluated to measure the maximum rate which the ceramic compositions of the invention may be heated. The maximum rate of heating of the samples is based on appearance of either surface cracks or internal melting and cracking. The results of these property measurements are presented in Tables 1–11. These properties show that the ceramic materials of the invention are useful in a variety of applications where rapid heating rates and property stability are important. For example, such materials may be employed in applications directed to low temperature drying and sterilization. Additional applications include high temperature heating elements, semiconductors, thermocouples, temperature detectors and the like.

The improved properties of the ceramic compositions of the present invention are useful for devices such as dryers or sterilizers where such properties are beneficial for optimum operation. As noted above, in order to avoid overheating or oxide formation on articles to be sterilized, an appropriate quantity of IR must be generated for uniform exposure to the entire article. Since articles such as medical tools (syringes, scalpels, dental drill bits, etc), table wear (forks, knives, spoons, plates, glasses, etc), tools for food processing, instruments for the care of the human body (hair, nails, teeth, eyes, etc.), and the like have different configurations as well as different materials of construction, the IR generated for sterilization of such articles must be sufficient to sterilize the relatively larger surfaces of the articles without overheating or deteriorating the relatively smaller surfaces or those portions of the article which are made of less IR resistant materials.

As noted above, the art recognized that a ceramic screen could be used as a transforming member in an attempt to reduce the intensity of the IR to moderate its effects on the articles to be sterilized, but this often results in non-uniform sterilization. To remedy this problem, the present invention utilizes a first transforming screen made of the rare earth chromium oxide ceramic material described above as formulation A, which screen is placed in between the source of radiation and the article to be sterilized, and a second screen placed with respect to the first screen as a refractor of IR therefrom and made from a ceramic material having the following composition:

FORMULATION B

| Component | Weight Percent |
|---|---|
| SiO₂ | 10–28 |
| Fe₂O₃ | 15–35 |
| CaO | up to 15 |
| Al₂O₃ | up to 3.5 |
| MgO | up to 3 |
| CuO | up to 2 |
| Cr₂O₃ | Remainder |

A sterilizer device 100 is illustrated in FIGS. 1–4. The device 100 includes an internal chamber which is accessible by a door 110 and into which is placed the articles to be sterilized. The appropriate controls 120 for the radiation sources and, if desired, the temperature of the chamber and a LED display 130, are provided in convenient locations on the front of the device.

Figure 2:
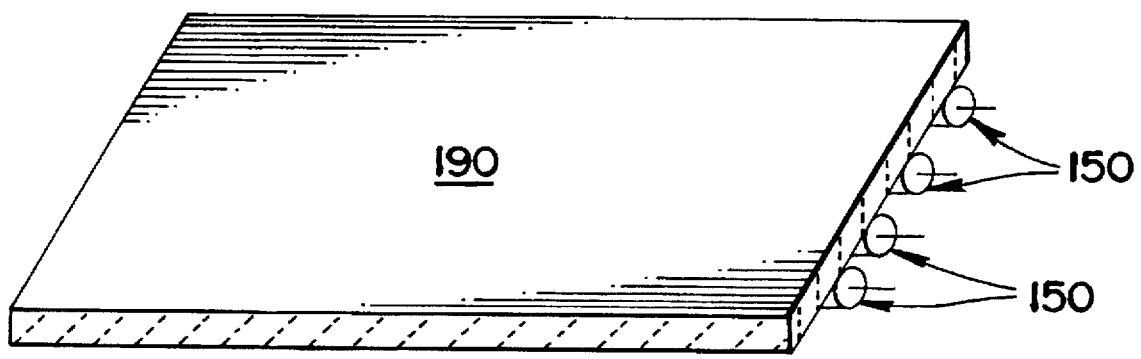
FIG. 2 is a view of an upper portion of the interior chamber of the sterilizer device of FIG. 1.
Figure 3:
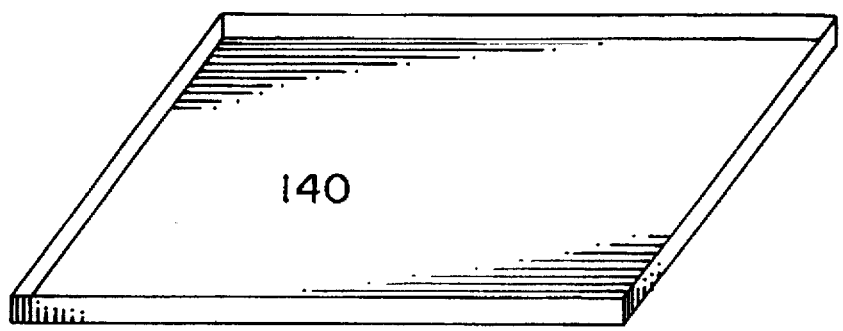
FIG. 3 is a view of a tray for holding articles to be sterilized in the device of FIG. 1.
Figure 4:
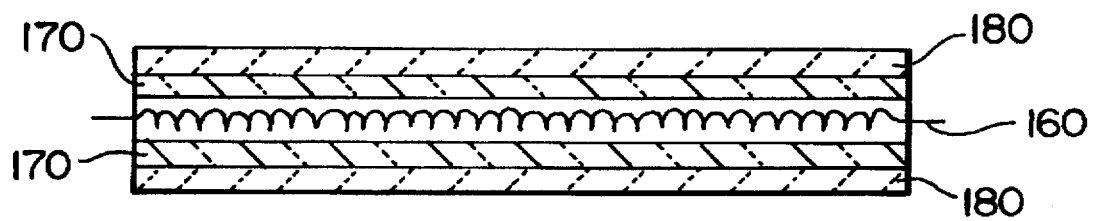
FIG. 4 is a side view, partially in cross-section of the energizing elements shown in FIG. 2.

In the chamber, as shown in FIGS. 2 and 3, a tray 140 is provided to support the articles to be sterilized. Located in an upper portion of the chamber are a number of energizable elements 150. These elements may be halogen lamps or a heating coil 160 of a high resistance material placed in a ceramic, quartz glass and/or metal tube 170.

In order to increase the sterilizing efficiency and to decrease the time of sterilization, these elements 150 are preferably provided with a concentric tube of a first ceramic material 180 for receiving and absorbing energy from the elements 150 and for emitting infrared radiation of one or more wavelengths, which radiation is subsequently directed toward the articles for sterilization thereof. This material 180 is preferably a ceramic material according to formulation A. In addition, a screen 190 of a second ceramic material, preferably a ceramic material according to formulation B, is placed above the elements for receiving and absorbing infrared radiation from the first ceramic material, and for emitting infrared radiation of one or more wavelengths which radiation is different from that emitted by the first ceramic material. This second ceramic material is positioned within the chamber so that its emitted radiation is directed toward the articles for sterilization thereof.

The ceramic compositions of the invention are also beneficial for use in drying devices. These devices have utility in a variety of applications, such as in the production of food products, plastics, ceramics, wood, bricks, leather, dishes, containers, pharmaceutical products and in other fields where it is necessary to have fast, efficient and qualitative drying with preservation of the main features of the objects that are to be dried.

Figure 5:
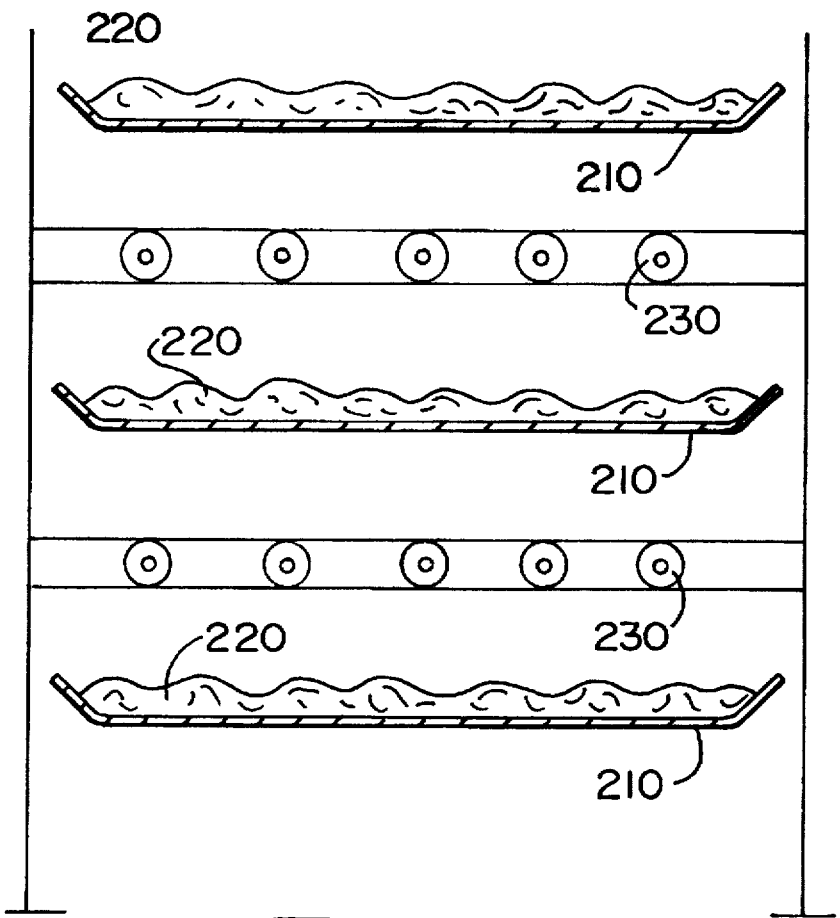
FIG. 5 is a view of the ceramic coated energizing elements and article support nets of a drying device of FIG. 1.
Figure 6:
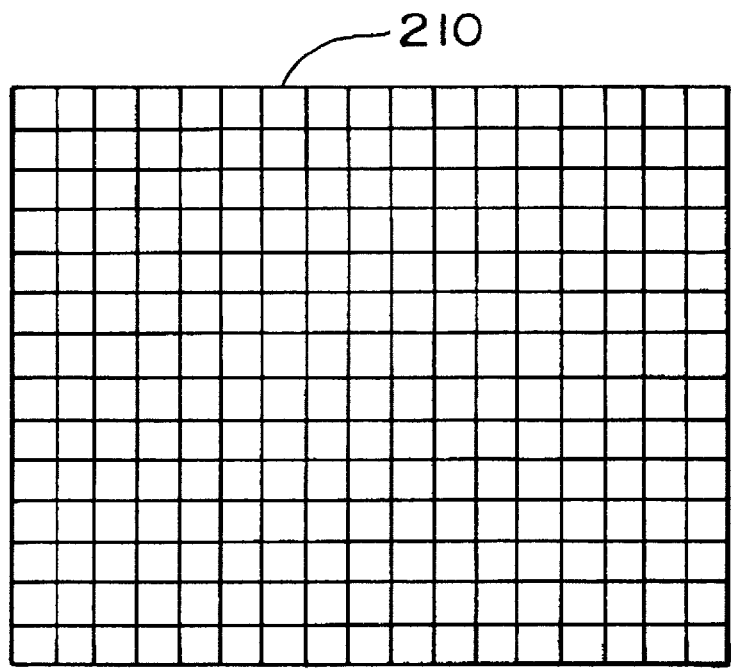
FIG. 6 is a top view of one of the support nets which hold articles to be dried in the device of FIG. 5.
Figure 7:
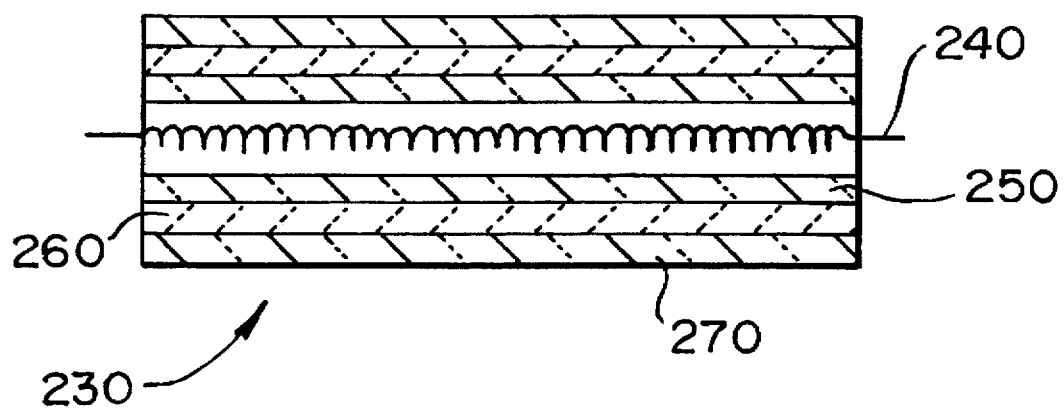
FIG. 7 is a side view, partially in cross-section of one of the energizing elements shown in FIG. 6.

One drying device is shown in FIGS. 5–7, wherein the device includes a drying chamber which it similar in external appearance to device 100 of FIG. 1. In the chamber of this device, a net or screen 210 is provided to support the objects 220 to be dried. Preferably, this net is made of a stainless steel wire mesh of suitable gauge to retain the objects to be dried thereupon. If desired, a plurality of such nets may be included within the chamber of the device. Disposed throughout the chamber are a number of energizable elements 230, as shown in FIGS. 5 and 7. These elements may be halogen lamps or a heating coil 240 of a high resistance material placed in a ceramic, quartz glass and/or metal tube 250. A transforming screen or coating of mullite or another aluminosilicate which includes a supplement of formulation A in an amount of 0.5–4.0% by weight of the composition is included within the chamber, placed adjacent the energizable elements for receiving and absorbing infrared radiation and for emitting infrared radiation of one or more wavelengths.

In another embodiment, it is possible to utilize energizable elements as disclosed above which are covered by a layer of first and second ceramic materials. In this regard, a first layer 260 of a ceramic composition, such as formulation B, is placed over the glass tube of the elements, and a second layer 270 of a ceramic composition, such as formulation A or a mixture of mullite with formulation A as defined above, is placed over the first layer 260. Preferred compositions for these ceramic layers are presented in the following examples.

Although the devices described above are specifically preferred embodiments, it should be realized that the size of the chamber, as well as the particular arrangement of the energizable elements and of the first and second ceramic materials therein, may be varied as desired by one skilled in the art, provided that a substantial portion of the infrared radiation emitted from both the first and second ceramic materials can be directed to the articles to be sterilized or dried. In addition, these devices can be used in a continuous mode, whereby the energizable elements are arranged about a conveyor belt or other movable support which carries the objects to be sterilized to, through and away from the radiation.

EXAMPLES

The invention is further described in connection with the following examples which are provided as illustrative, non-limiting embodiments thereof.

Examples 2–10 show the unexpected results obtainable with the ceramic compositions of the invention compared to a representative prior art ceramic composition (i.e., Example 1).

Example 1

(Control)

A ceramic composition with the following weight percentage components which are outside of the percent ranges of the compositions of the invention is formulated as follows:

| Component | Weight Percent |
|---|---|
| $LaCrO_3$ | 98.55 |
| $MgCrO_4$ | 0.5 |
| $MgAl_2O_4$ | 0.3 |
| $YCrO_3$ | 0.3 |
| $ZrO_2$ | 0.3 |
| $CeO_2$ | 0.05 |
| $CaZrO_3$ | 0.03 |

These components are mixed and ground in a plastic lined planet mill with Teflon balls. The resulting powder is dried, melted, re-ground and then pressed into samples having dimensions of 50×6×6 mm in the middle portion and 50×6×12 mm at the end portions for use in evaluating the maximum heating rate of the ceramic. Samples measuring 40×4×4 mm for measurement of specific resistance, and samples measuring 15 mm diameter and 15 mm high for measurement of weight loss and compressive strength were also prepared. Each of these samples is sintered in a furnace with $LaCrO_3$ heating elements at about 1600° C. for about 12 hours in air. The resulting, sintered materials then are heated for about 60 hours at about 1500° C. to evaluate compressive strength at that temperature, or for about 20 hours at about 1600° C. to evaluate weight loss.

Samples for evaluation of maximum heating rate are heated at a variety of rates. Cross-sections of these samples are inspected to identify surface cracks and internal melting. Samples heated at a rate of 5 K/min were found to be in good condition. Samples heated at a rate of 10 K/min showed cracking. As shown in Table 1, the properties of Control Example 1 given in column 1 therein are inferior to the properties of the ceramics disclosed in U.S. Pat. No. 3,475,352 given in column 6 of Table 1.

Example 2

The procedure of control Example 1 is followed with the exception that the ceramic composition employed corresponds to that of column 2 of Table 1. The resulting products have properties which surprisingly are superior to the properties of the products of U.S. Pat. No. 3,475,352 shown in column 6 of Table 1.

Example 3

The procedure of control Example 1 is followed with the exception that the ceramic composition corresponds to that of column 3 of Table 1. As shown in Table 1, the properties of the samples produced are surprisingly better than that of U.S. Pat. No. 3,475,352. Illustratively, the decrease in the compressive strength after about 60 hours of exposure at about 1500° C. is only 4.2 MPa. Further, the maximum heating rate is five times greater than that disclosed in U.S. Pat. No. 3,475,352.

Example 4

The procedure of control Example 1 is followed with the exception that the ceramic composition corresponds to Column 4 of Table 1. As shown in Table 1, the properties of the samples produced are better than those of U.S. Pat. No. 3,475,352 with the exception of specific resistance.

Example 5

The procedure of control Example 1 is followed with the exception that the ceramic composition corresponds to column 5 of Table 1. The increase in specific resistance of this example surprisingly is so great that the sample was unable to be heated to evaluate maximum heating rate.

Example 6

The procedure of control Example 1 is followed with the exception that the compositions shown in columns 1–5 of Tables 2 and 3 are employed. In the compositions of Table 2, minimal percentages of $MgAl_2O_4$ are employed whereas in Table 3, maximal amounts $MgAl_2O_4$ are employed. As can be seen from the data presented in Tables 2 and 3, the properties shown in columns 2–5 of Tables 1 and 2 exceed those of U.S. Pat. No. 3,475,352.

Example 7

The procedure of control Example 1 is followed with the exception that the compositions shown in columns 1–5 of Tables 4 and 5 are employed. In the compositions of Table 4, minimal amounts of $YCrO_3$ are employed whereas in Table 5 maximal amounts of $YCrO_3$ are employed. As shown in Tables 4 and 5, the properties of the inventive compositions shown in columns 2–5 exceed those of U.S. Pat. No. 3,475,352.

Example 8

The procedure of control Example 1 is followed with the exception that the compositions shown in columns 1–5 of Tables 6 and 7 are employed. In the compositions of Table 6, minimal amounts of $MgCr_2O_4$ are employed whereas maximal amounts of $MgCr_2O_4$ are employed in Table 7. As shown in Tables 6 and 7, the properties of the inventive compositions shown in columns 2–5 exceed those of U.S. Pat. No. 3,475,352.

Example 9

The procedure of control Example 1 is employed with the exception that the compositions shown in columns 1–5 of Tables 8 and 9 are employed. In the compositions of Table 8, minimal amounts of $CeO_2$ are employed whereas maximal amounts of $CeO_2$ are employed in Table 9. As shown in Tables 8 and 9, the properties of the inventive compositions shown in columns 2–5 exceed those of U.S. Pat. No. 3,475,352.

Example 10

The procedure of control Example 1 is employed with the exception that the compositions shown in Tables 10 and 11 are employed. In the compositions of Table 10, minimal amounts of $CaZrO_3$ are employed whereas maximal amounts of $CaZrO_3$ are employed in Table 11. As shown in columns 2–5 of Tables 10 and 11, the properties of the inventive compositions of Example 10 exceed those of U.S. Pat. No. 3,475,352.

As the foregoing examples of the invention illustrate, the invention surprisingly provides reductions in weight loss of up to three times more than that of the prior art. The invention further surprisingly provides a nine-fold decrease in the variation of compressive strength under pressure after exposure at about 1500° C. for about 60 hours. The invention moreover provides nearly an increase of 1.5 times the compressive strength and a five fold increase in the maximal rate of heating.

TABLE 1

| Components and properties | Percentage of components, weight % | | | | | |
|---|---|---|---|---|---|---|
| | 1 | 2 | 3 | 4 | 5 | 6[3] |
| $MgAl_2O_4$ | 0.3 | 0.5 | 3.0 | 10.0 | 12.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | BALANCE | | | | | |
| Weight loss, % | 1.2 | 0.5 | 0.2 | 0.3 | 1.0 | 0.55–0.6 |
| Specific resistance, (Ohm-cm) | 292.1 | 116.0 | 7.7 | 873.4 | 2213.4 | 50–4800 |
| $\sigma Pa^1$ | 72.6 | 96.3 | 144.1 | 120.1 | 115.6 | 96–135 |
| $\sigma Pa^2$ | 18.4 | 71.4 | 140.3 | 33.2 | 26.2 | 10.2–16.1 |
| Maximal speed of heating K/min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 2

| Components and main parameters | Percentage of components, weight % | | | | | |
|---|---|---|---|---|---|---|
| | 1 | 2 | 3 | 4 | 5 | 6 |
| $MgAl_2O_4$ | 0.5 | 0.5 | 0.5 | 0.5 | 0.5 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | BALANCE | | | | | |
| Weight loss, % | 1.0 | 0.5 | 0.2 | 0.3 | 1.0 | 0.55–0.6 |
| Specific resistance, (Ohm-cm) | 304.8 | 116.0 | 7.4 | 672.3 | 1995.9 | 50–4800 |
| $\sigma Pa^1$ | 74.2 | 96.3 | 136.2 | 118.1 | 110.4 | 96–135 |
| $\sigma Pa^2$ | 18.7 | 71.4 | 130.5 | 33.1 | 25.1 | 10.2–16.1 |
| Maximal speed of heating K/min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 3

| Components and main parameters | Percentage of components, weight % | | | | | |
|---|---|---|---|---|---|---|
| | 1 | 2 | 3 | 4 | 5 | 6 |
| $MgAl_2O_4$ | 10.0 | 10.0 | 10.0 | 10.0 | 10.0 | |
| $YCrO_3$ | 0.3 | 0.5 | 1.5 | 3.0 | 4.0 | |
| $MgCr_2O_4$ | 0.5 | 1.0 | 10.0 | 15.0 | 20.0 | |
| $CeO_2$ | 0.05 | 0.1 | 0.5 | 1.0 | 2.0 | |
| $ZrO_2$ | 0.3 | 0.5 | 3.0 | 5.0 | 6.0 | |
| $CaZRO_3$ | 0.03 | 0.05 | 0.3 | 0.5 | 0.6 | |
| $LaCrO_3$ | BALANCE | | | | | |
| Weight loss, % | 1.2 | 0.5 | 0.2 | 0.3 | 1.0 | 0.55–0.6 |

TABLE 3-continued

| Components and main parameters | Percentage of components, weight % | | | | | |
|---|---|---|---|---|---|---|
| | 1 | 2 | 3 | 4 | 5 | 6 |
| Specific resistance, (Ohm-cm) | 490.3 | 399.7 | 55.2 | 837.4 | 1857.8 | 50–4800 |
| σPa[1] | 112.6 | 98.8 | 152.8 | 120.1 | 103.2 | 96–135 |
| σPa[2] | 29.6 | 81.4 | 143.2 | 33.2 | 38.6 | 10.2–16.1 |
| Maximal speed of heating K/min | 5 | 15 | 50 | 20 | — | 10 |

[1] Room Temperature Compressive Strength
[2] Compressive Strength after 60 hours exposure at 1500° C.
[3] Properties of U.S. Pat. No. 3,475,352

TABLE 4

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.5 | 0.5 | 0.5 | 0.5 | 0.5 | |
| MgCr$_2$O$_4$ | 0.5 | 1.0 | 10.0 | 15.0 | 20.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | BALANCE | | | | | |
| Weight loss, % | 1.2 | 0.5 | 0.2 | 0.3 | 1.0 | 0.55–0.6 |
| Specific resistance, (Ohm-cm) | 270.5 | 116.0 | 35.1 | 819.5 | 2035.7 | 50–4800 |
| σPa[1] | 72.6 | 96.3 | 144.1 | 120.1 | 115.6 | 96–135 |
| σPa[2] | 18.4 | 71.4 | 140.3 | 33.2 | 26.2 | 10.2–16.1 |
| Maximal speed of heating K/min | 5 | 15 | 50 | 20 | — | 10 |

[1] Room Temperature Compressive Strength
[2] Compressive Strength after 60 hours exposure at 1500° C.
[3] Properties of U.S. Pat. No. 3,475,352

TABLE 5

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 3.0 | 3.0 | 3.0 | 3.0 | 3.0 | |
| MgCr$_2$O$_4$ | 0.5 | 1.0 | 10.0 | 15.0 | 20.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | BALANCE | | | | | |
| Weight loss, % | 1.2 | 0.5 | 0.2 | 0.3 | 1.0 | 0.55–0.6 |
| Specific resistance, (Ohm-cm) | 353.8 | 220.3 | 25. | 873.4 | 2213.4 | 50–4800 |
| σPa[1] | 82.7 | 93.7 | 121.2 | 120.1 | 125.8 | 96–135 |
| σPa[2] | 19.9 | 62.8 | 87.3 | 33.2 | 28.7 | 10.2–16.1 |
| Maximal speed of heating K/min | 5 | 15 | 40 | 20 | — | 10 |

[1] Room Temperature Compressive Strength
[2] Compressive Strength after 60 hours exposure at 1500° C.
[3] Properties of U.S. Pat. No. 3,475,352

TABLE 6

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 1.0 | 1.0 | 1.0 | 1.0 | 1.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | BALANCE | | | | | |
| Weight loss, % | 1.2 | 0.5 | 0.2 | 0.3 | 1.0 | 0.55–0.6 |
| Specific resistance, (Ohm-cm) | 188.5 | 116.0 | 18.0 | 867.1 | 2055.7 | 50–4800 |
| σPa[1] | 92.5 | 96.3 | 117.8 | 102.3 | 98.7 | 96–135 |
| σPa[2] | 37.4 | 51.4 | 60.3 | 21.1 | 13.1 | 10.2–16.1 |
| Maximal speed of heating K/min | 5 | 15 | 40 | 20 | — | 10 |

[1] Room Temperature Compressive Strength
[2] Compressive Strength after 60 hours exposure at 1500° C.
[3] Properties of U.S. Pat. No. 3,475,352

TABLE 7

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 15.0 | 15.0 | 15.0 | 15.0 | 15.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | BALANCE | | | | | |
| Weight loss, % | 1.2 | 0.5 | 0.2 | 0.3 | 1.0 | 0.55–0.6 |
| Specific resistance, (Ohm-cm) | 282.0 | 199.0 | 22.1 | 873.4 | 2076.5 | 50–4800 |
| σPa[1] | 87.3 | 96.3 | 98.1 | 120.1 | 105.3 | 96–135 |
| σPa[2] | 81.2 | 90.6 | 90.3 | 33.2 | 25.1 | 10.2–16.1 |
| Maximal speed of heating K/min | 5 | 15 | 30 | 20 | — | 10 |

[1] Room Temperature Compressive Strength
[2] Compressive Strength after 60 hours exposure at 1500° C.
[3] Properties of U.S. Pat. No. 3,475,352

TABLE 8

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 0.5 | 1.0 | 10.0 | 15.0 | 20.0 | |
| CeO$_2$ | 0.1 | 0.1 | 0.1 | 0.1 | 0.1 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | | | BALANCE | | | |
| Weight loss, % | 1.2 | 0.5 | 0.2 | 0.3 | 1.0 | 0.55–0.6 |
| Specific resistance, (Ohm-cm) | 297.0 | 116.0 | 8.1 | 862.1 | 2098.9 | 50–4800 |
| σPa$^1$ | 72.6 | 96.3 | 144.0 | 120.3 | 115.0 | 96–135 |
| σPa$^2$ | 18.4 | 71.4 | 140.3 | 33.2 | 26.2 | 10.2–16.1 |
| Maximal speed of heating K/min | 10 | 15 | 40 | 20 | — | 10 |

[1]Room Temperature Compressive Strength
[2]Compressive Strength after 60 hours exposure at 1500° C.
[3]Properties of U.S. Pat. No. 3,475,352

TABLE 9

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 0.5 | 1.0 | 10.0 | 15.0 | 20.0 | |
| CeO$_2$ | 1.0 | 1.0 | 1.0 | 1.0 | 1.0 | |
| ZrO$_2$ | 0.3 | 0.5 | 3.0 | 5.0 | 6.0 | |
| CaZRO$_3$ | 0.03 | 0.05 | 0.3 | 0.5 | 0.6 | |
| LaCrO$_3$ | | | BALANCE | | | |
| Weight loss, % | 1.2 | 0.5 | 0.2 | 0.3 | 1.0 | 0.55–0.6 |
| Specific resistance, (Ohm-cm) | 288.0 | 110.2 | 10.6 | 873.4 | 2398.1 | 50–4800 |
| σPa$^1$ | 71.9 | 89.3 | 134.5 | 120.1 | 107.6 | 96–135 |
| σPa$^2$ | 16.7 | 67.5 | 112.4 | 33.2 | 21.5 | 10.2–16.1 |
| Maximal speed of heating K/min | 5 | 15 | 40 | 20 | — | 10 |

[1]Room Temperature Compressive Strength
[2]Compressive Strength after 60 hours exposure at 1500° C.
[3]Properties of U.S. Pat. No. 3,475,352

TABLE 10

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 0.5 | 1.0 | 10.0 | 15.0 | 20.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.05 | 0.05 | 0.05 | 0.05 | 0.05 | |
| LaCrO$_3$ | | | BALANCE | | | |
| Weight loss, % | 0.9 | 0.5 | 0.3 | 0.4 | 1.0 | 0.55–0.6 |
| Specific resistance, (Ohm-cm) | 348.0 | 116.0 | 6.6 | 717.8 | 1857.0 | 50–4800 |
| σPa$^1$ | 92.6 | 96.3 | 123.1 | 103.3 | 89.8 | 96–135 |
| σPa$^2$ | 21.3 | 71.4 | 101.6 | 36.9 | 32.2 | 10.2–16.1 |
| Maximal speed of heating K/min | 5 | 15 | 50 | 20 | — | 10 |

[1]Room Temperature Compressive Strength
[2]Compressive Strength after 60 hours exposure at 1500° C.
[3]Properties of U.S. Pat. No. 3,475,352

TABLE 11

| Components and main parameters | Percentage of components, weight % | | | | | |
|---|---|---|---|---|---|---|
| | 1 | 2 | 3 | 4 | 5 | 6 |
| MgAl$_2$O$_4$ | 0.3 | 0.5 | 3.0 | 10.0 | 12.0 | |
| YCrO$_3$ | 0.3 | 0.5 | 1.5 | 3.0 | 4.0 | |
| MgCr$_2$O$_4$ | 0.5 | 1.0 | 10.0 | 15.0 | 20.0 | |
| CeO$_2$ | 0.05 | 0.1 | 0.5 | 1.0 | 2.0 | |
| ZrO$_2$ | 0.3 | 0.5 | 3.0 | 5.0 | 6.0 | |
| CaZRO$_3$ | 0.5 | 0.5 | 0.5 | 0.5 | 0.5 | |
| LaCrO$_3$ | | | BALANCE | | | |
| Weight loss, % | 0.3 | 0.3 | 0.2 | 0.3 | 1.0 | 0.55–0.6 |
| Specific resistance, (Ohm-cm) | 396.0 | 275.1 | 54.0 | 873.4 | 1985.0 | 50–4800 |
| σPa$^1$ | 96.6 | 112.3 | 152.1 | 120.1 | 109.7 | 96–135 |
| σPa$^2$ | 16.2 | 61.2 | 121.4 | 33.2 | 30.2 | 10.2–16.1 |
| Maximal speed of heating K/min | 5 | 15 | 30 | 20 | — | 10 |

[1]Room Temperature Compressive Strength
[2]Compressive Strength after 60 hours exposure at 1500° C.
[3]Properties of U.S. Pat. No. 3,475,352

The following example illustrates the use of the present ceramic compositions in a sterilization device as described above.

Example 11

Articles of medical instruments in need of sterilization were put into a chamber having the dimensions 310×175×100 mm. As a source of IR radiation, four halogen lamps were used, and these were uniformly distributed in the upper part of the chamber. The lamps are additionally covered by a layer of ceramic material of formulation A.

Above the lamps was placed a screen prepared from the ceramic material of formulation B. After turning on the power, the transforming layers begin to be heated and after a time of 1–1.5 min., the temperature of the transforming layers becomes stabilized due to thermal balance at the approximate level of 600 degrees C. In such way, the treatment of the medical instruments takes place through the IR radiation.

Results of the sterilization tests were as follows. Various medical instruments such as syringes and needles, scarificators, scalpels and pincers were then exposed to IR at 125° C. using the sterilizing device of the invention for time periods of 1, 2, 3, 5, 10 and 15 minutes, respectively. Nine separate tests were conducted for each article at each time period. It was found that each of the articles was appropriately sterilized with no indication of bacteria or viruses.

A second round of tests were conducted on the same articles for the same degree of IR and at the same time period and temperatures. Again, nine tests were made for each article at each time period. Investigations show high efficiency and reliability of the method of sterilization suggested here. It was again found that each of the articles was appropriately sterilized with no indication of antigens, HB or hepatitis B by the ROPGA method.

In comparison, the use of a prior art sterilizer device which did not include ceramic screens did not sterilize and of the 72 articles tested in the same manner as above. When the articles were properly sterilized by exposure to the IR for a period of greater than 15 minutes, many of the syringes cracked and a number of the metal articles became discolored due to local overheating of those portions of the articles.

The following example illustrates the use of the present ceramic compositions in a drying device as described above.

Example 12

An object in need of drying is prepared in accordance with its type, for example vegetables and fruits could be washed, cleaned from any rotting parts, cut if necessary and then put into the chamber of the dryer described above and then exposed to IR radiation, where the IR radiation is produced by the action of radiation of a primary source into a transforming layer or screen of the ceramic material of formulation B. As a primary source of radiation the energizable elements described above can be used.

The drying process continues until the decrease of the product mass stops. The cell mass of the product is preserved under the drying process without destruction and/or alteration. This allows the preservation of most primary property and feature of the dried product, such as its nutritious properties or features, including color, taste, smell, etc. At same time the product is dried, it is also sterilized.

When the dried product is placed into water, it takes about 15–25 minutes to re-absorb the lost water and restore its primary shape and condition, i.e. the volume, weight, taste, smell, etc.

In order to perform comparative analysis of different materials we have developed an experimental device, consisting of radiators disposed in the bottom side and a net made of stainless steel 200 mm above the radiators. The product to be dried is placed on the net.

Carrots, cut in the shape of straws with the approximate sizes of 5×5×60 mm, are exposed to a density of radiated energy (in electric power) of 3 KW/m². Drying results on these products are compared using the following elements:

(1) a conventional heat coil made of nichrome wire in a quartz glass tube,
(2) a heat coil which is covered by a layer of mullite,
(3) a heat coil which is covered by a single layer of a ceramic material in accordance with one embodiment of the present invention,
(4) a heat coil which is covered by a single layer of a ceramic material in accordance with an another embodiment of the present invention, and
(5) a heat coil which is covered by a dual layer of ceramic material in accordance with yet another embodiment of the present invention.

The ceramic layer of element (3) included the following composition:

| Formulation C | |
|---|---|
| Component | Weight Percent |
| $Fe_2O_3$ | 28 |
| $SiO_2$ | 17 |
| CaO | 5.5 |
| $Al_2O_3$ | 2.5 |
| MgO | 2 |
| CuO | 0.3 |
| $Cr_2O_3$ | 44.7 |

The ceramic layer of element (4) included 1% by weight of the ceramic material of formulation 2 of Table 1 with 99% by weight of mullite ("formulation D"), while the ceramic layer of element (5) included a first layer of the ceramic composition of formulation C, followed by a second layer of the ceramic material of formulation D.

Figure 8:
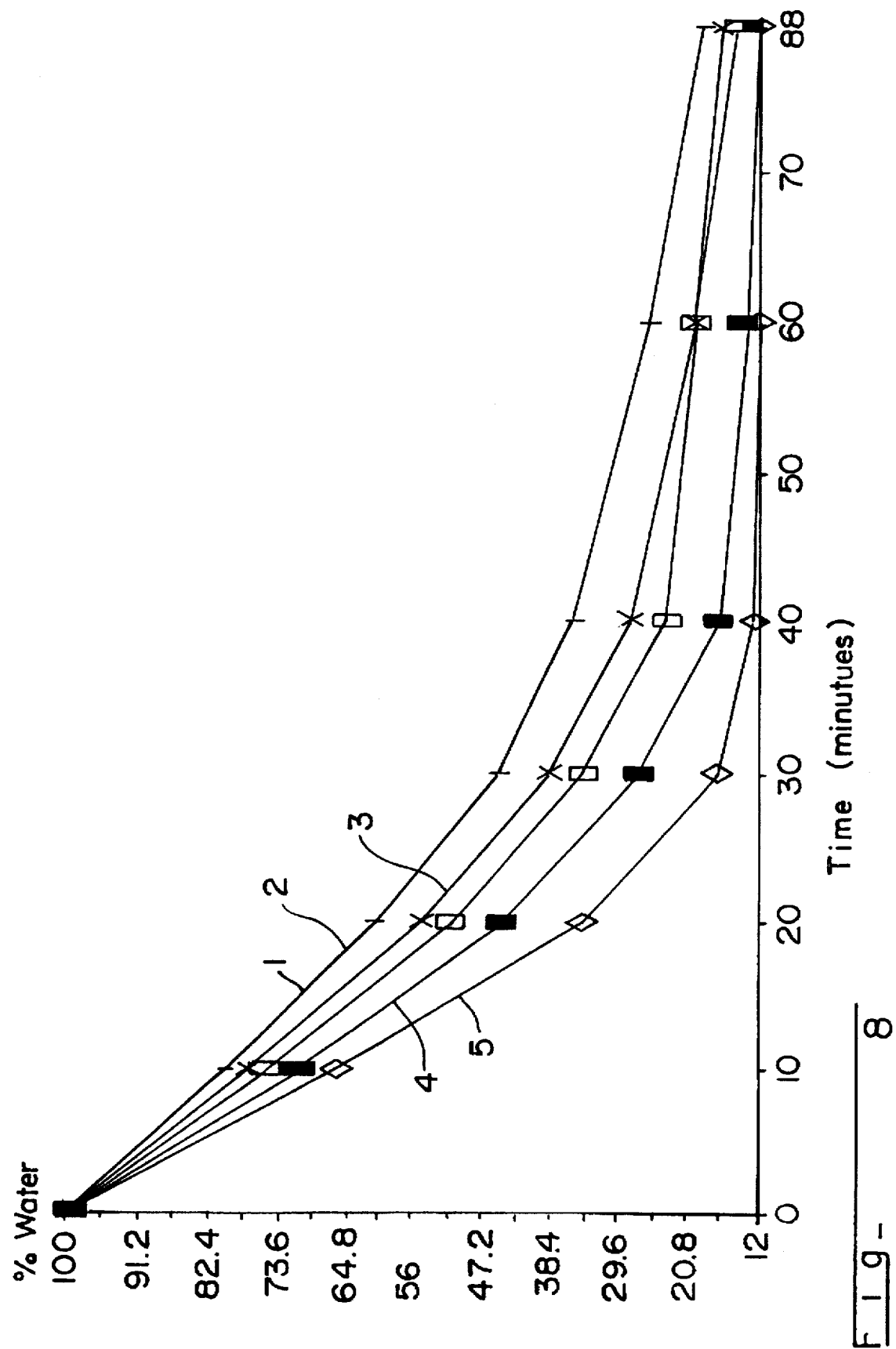
FIGS. 8–9(a) and (b) are graphical representations of drying results utilizing a device which incorporates dual ceramic compositions of the invention.

The various formulations having a particle size of about 1 micron were applied as a coating onto the surface of the elements using a brush together with glue made of polyvinyl spirits and/or fluid glass. Then, the elements were put into the drying device for testing. The results obtained are shown in FIG. 8.

As follows from the data presented, the maximum speed of the drying process is achieved by the consequential covering of the radiators with the two ceramic compositions (element (5)). In this case, the product being dried approaches a constant weight after about 40 minutes. Element (4) also produces a dried product after about 75 minutes. These elements have a higher drying efficiency than conventional IR drying devices.

Additional drying results on these products are compared using the following elements:

(6) a heat coil which is covered by a single layer of a ceramic material in accordance with one embodiment of the present invention,
(7) a heat coil which is covered by a layer of mullite,
(8) a heat coil which is covered by a single layer of a ceramic material in accordance with another embodiment of the present invention, and
(9) a heat coil which is covered by a dual layer of ceramic material in accordance with yet another embodiment of the present invention.

The ceramic layer of element (6) included the following composition:

| Formulation E | |
|---|---|
| Component | Weight Percent |
| $Fe_2O_3$ | 35 |
| $SiO_2$ | 28 |
| CaO | 15 |
| $Al_2O_3$ | 3.5 |
| MgO | 3 |
| CuO | 2 |
| $Cr_2O_3$ | 13.5 |

The ceramic layer of element (8) included 1% by weight of the ceramic material of formulation 4 of Table 11 with 99% by weight of mullite ("formulation F"), while the ceramic layer of element (9) included a first layer of the ceramic composition of formulation E, followed by a second layer of the ceramic material of formulation F.

Figure 9:
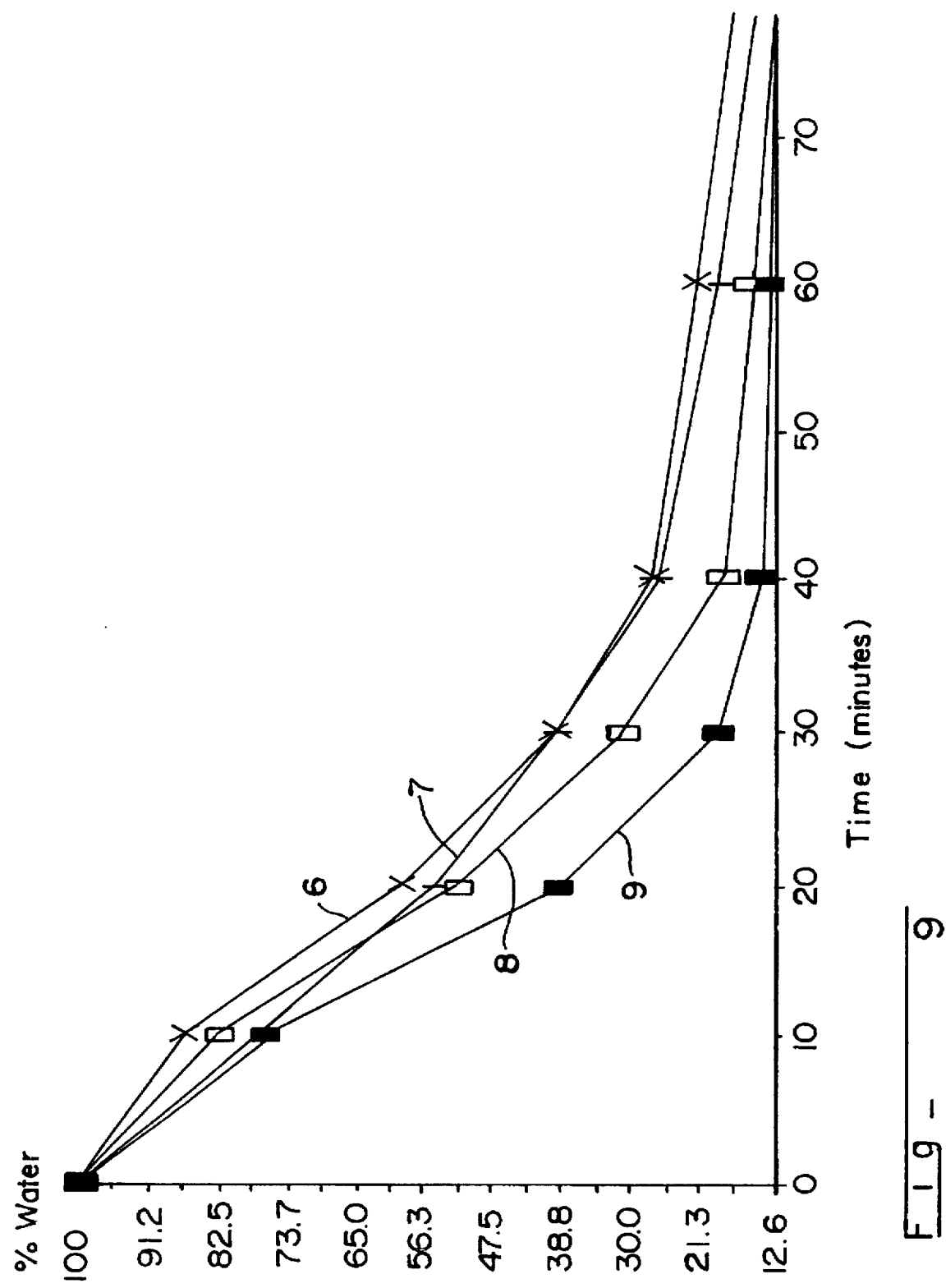

The various formulations having a particle size of about 1 micron were applied as described above, and the elements were put into the drying device for testing. The results obtained are shown in FIG. 9.

Again, the maximum speed of the drying process is achieved by the consequential covering of the radiators with the two ceramic compositions (element (9)), with the product being dried approaching a constant weight after about 40 minutes. Element (8) also produces a dried product after about 75 minutes. These elements have a higher drying efficiency than conventional drying devices.

Moreover, independent tests of dried carrots show that the present invention possess high organoleptic properties with maximum preservation of the such properties and features of the carrots, including their nutritional value and general/overall appearance in comparison with carrots dried by previously known methods.

IR radiation generated by ceramic materials in accordance with the inventions may be employed in a wide variety of further applications such as silk manufacture, preservation of bio-materials, drying of thermoplastics, food preservation, seed preservation, baking of foodstuffs, cooking of foodstuffs, aging of wines, water desalination and of drying of coatings such as paints. These applications are illustrated below.

Silk Manufacture

IR radiation generated in accordance with the invention may be used in silk cocoon processing facilities as well as in the biotechnology industry. In silk manufacture, it is known to dry live silkworm pupae and live cocoons by sublimation. Sublimation provides cocoons with satisfactory properties while retaining their nativity; nevertheless, this method is not widely accepted and is too expensive to be used on an industrial scale.

A commercial method of drying silkworm pupae and cocoons employs convective heat. See Sh. Yuldashev, I. Z. Burnashev, U. Baturov, A. Karimov, E. Tajiyev. "Efficiency of moistening the heat carrier in cocoon driers". Report 3, Comparative testing of cocoon driers. "Sholk (silk)," #3, p. 19, 1990. This method, however, yields pupae with poor properties and virtually is not used in biotechnological practice. Drying live pupae and live cocoons has also been performed by UHF-microwave with vacuuming. This method, however, is also expensive and has not yet found widespread industrial application. See B Ya. Khaimov et al., "Efficiency of moistening the heat carrier in cocoon driers", report 3. Comparative testing of cocoon driers. "Sholk(silk)," #3, p. 19, 1990.

Drying of silkworm pupae and cocoons by IR radiation generated in accordance with the invention, however, surprisingly provides improved properties in the ease and speed of unwinding cocoons, as well as in the resulting raw silk material. Drying by IR radiation in accordance with the invention also preserves the nativity of the pupae and cocoons so that the pupae can be used in biotechnical and other applications.

Generally, treatment of cocoons according to the invention is achieved by exposing live cocoons to infrared (IR) radiation generated by the ceramic compositions A and B defined above. This is explained in further detail by the following, non-limiting examples.

Example 13

Figure 10A:
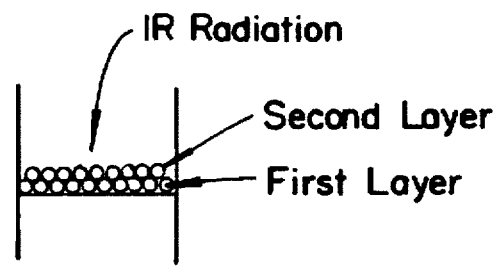
FIG. 10(a) and (b) are schematic illustrations of drying various configurations of layers of silkworm cocoons and pupae by IR radiation.

Live silkworm cocoons are placed on a woven-wire tray in two vertically stacked layers as shown in FIG. 10(a). The cocoons are subjected to IR radiation generated by a ceramic transforming screen formed of a composition of a mixture of 1% of composition A and 99% mullite. The cocoons are subjected to IR radiation generated by the ceramic screen under conditions of natural convective ventilation and without temperature control. The temperature of the ceramic screen employed to generate the IR is 180°–200° C. The time of treatment is in accordance with FIG. 11. The properties of silk derived from cocoons dried in accordance with this example is shown in Table 12.

Example 14

Figure 10B:
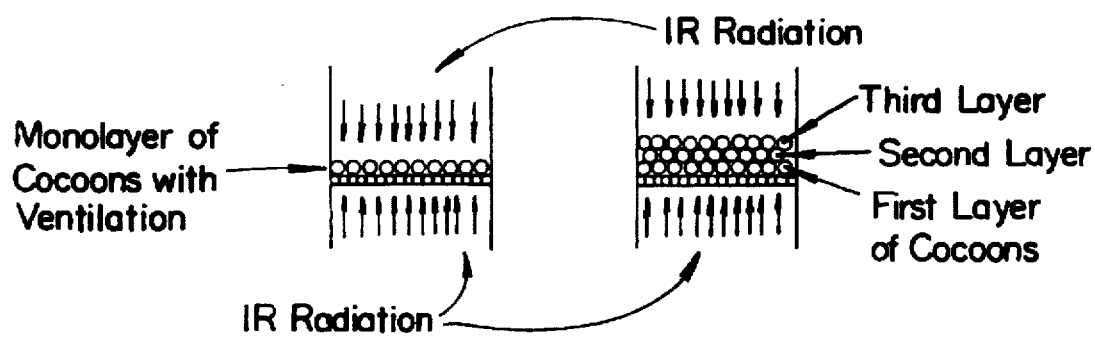

As shown in FIG. 10(b), live silkworm cocoons are placed in a 'monolayer', and in a vertical stack of three layers on separate woven-wire trays. The cocoons are exposed to IR radiation generated as in Example 13. A mode of forced ventilation, however, is used so that the temperature of the cocoons does not exceed 50° C.±0.5° C.

Figure 11:
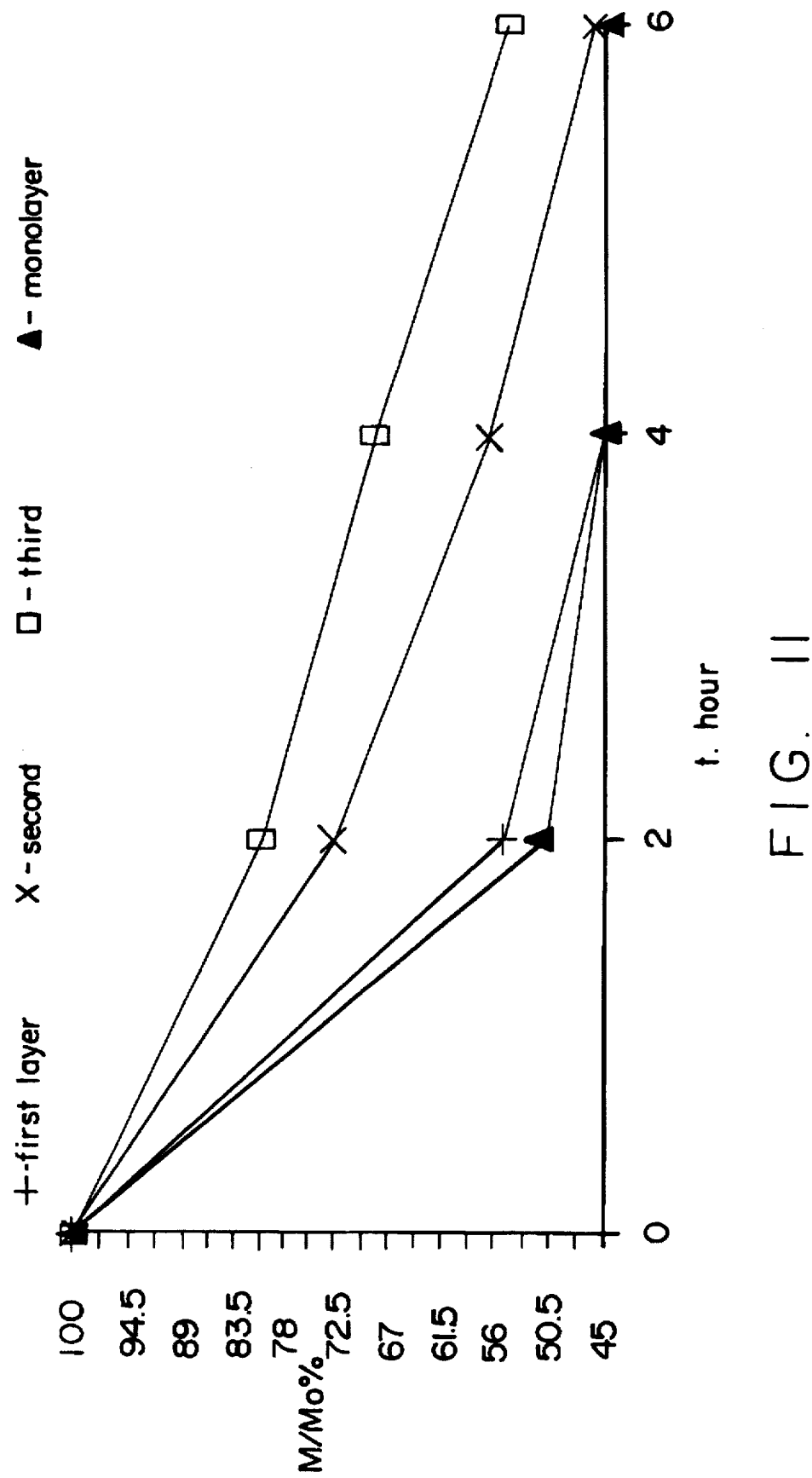
FIG. 11 shows the rate of drying of the layers of cocoons illustrated in FIGS. 10(a) and (b).

Drying by the IR radiation generated by the ceramic screen formed of formulations A and B(mullite) above are shown in FIG. 11. As shown, the 'monolayer' of cocoons dries more rapidly than the top layer in the tri-layer stack. The middle and bottom layers of the stack dry more slowly. Drying is significantly accelerated by ventilation.

The cocoons produced are unwound into silk. The properties of silk derived from cocoons dried in accordance with this example are shown in Table 12. Compared to conventional UHF drying and convection heat drying and as can be seen from Table 12, drying of cocoons according to the invention increases the output of raw silk, decreases the amount of total waste, reduces the extent of thread discontinuities (which contributes to increasing the length of the continuously unwound thread), increases the extent and speed of unwinding of the cocoons, as well as the total length of thread per cocoon.

Unwinding of the cocoons is measured in a machine manufactured by "Shin Masuzawa Co., Ltd." designed to individually unravel cocoons. Details of the machine are discussed in B. YS. Kahimov et al., "A Study of the Properties of Cocoons Dried in an UHF Field in Cocoon Dryers," Electronika TKSH-50, Report 3, Effect of Processing Parameters in the Cocoon Drier Electronika TKSH-50 an the Technological Properties of Cocoons" SHOLK (SILK) N3, pp. 21–23, 1985. For comparison, and as shown in Table 12, cocoons dried by conventional convective heat drying at 120° C., for 4–8 hours are unwound at 85 m/min at an average thread breakage of 1.8 per cocoon. Cocoons dried by the UHF method when unwound at the same speed, had an average thread breakage of 0.75. Surprisingly, however, cocoons dried according to the invention could be unwound at a speed of 240 m/min at an average thread breakage of only 0.8.

Cocoons dried according to the methods given above also are evaluated for biological activity. For evaluating the biological activities, we evaluated several fermentative activities which have been previously studied on the silkworm and which have different thermal stabilities. These fermentative activities included phospholipase A2, as well as the trypsin and chymotrypsin inhibitors as measured on specific synthetic ether substrates (BASE and ATEE).

Tables 13 and 14 summarize the results of fermentation tests performed on various samples of silkworm pupae. As can be seen from these tables, the lowest phospholipase A2 activity corresponds to pupae obtained from cocoons dried by the aforementioned convective heat drying method. See Sh. Yuldashev, I. Z. Burnashev, U. Baturov, A. Karimov, E. Tajiyev. "Efficiency of moistening the heat carrier in cocoon driers". Report 3. Comparative testing of cocoon driers.

"Sholk (silk)," #3, p. 19, 1990. Drying by IR radiation generated as in the invention, however, yields results nearly equal to those of the much more expensive sublimation drying. Also, as shown in Table 14, drying in accordance with the invention enables the pupae to retain even the normally low proteolytical activities of the silkworm, i.e., trypsin-type and chymotrypsin-type activities. Retention of these activities is clear from a sharp increase in the initial trypsin and chymotrypsin activity upon incubation of these enzymes with extracts of pupae dried in accordance with the invention. A similar retention of activity and stability of other enzymes, unsaturated lipids, and vitamins treated with extracts of pupae dried in accordance with the invention is observed.

TABLE 12*

| Method of Drying | Yield Raw Silk % | Yield of Cocoon Skin % | Yield of Film % | Total Product as % of Total Weight | Average Tread Breakage per Cocoon | Length of the Continuously Unwound Thread | Extent of Unwinding % | Speed of Unwinding | Total Length of the Thread/ Cocoo ) |
|---|---|---|---|---|---|---|---|---|---|
| Convective heat drying[1] | | | | | 1.8 | | | 85 | |
| UHF drying | 32.1 | 4.9 | 8.2 | 45.2 | 0.75 | 576 | 73.4 | 85 | 904 |
| IR drying (Ex. 13) | 34.2 | 3.9 | 7.7 | 45.8 | 0.8 | 638 | 74.6 | 240? | 1124 |
| IR drying (Ex. 14) | 36.8 | 2.3 | 6.9 | 46.0 | 0.8 | 817 | 79.8 | 240? | 1229 |

*This table lists the averaged data of three successive runs of 90 cocoons (for UHF drying) and of 60 cocoons (for IR drying in accordance with the invention)
[1]120° C., time = 4–8 hours;
[2]B. Ys. Khaimov, et al. "A study of the properties of cocoons dried in an UHF field in cocoon driers 'Elektronika TKSh-50'." Report 3. Effect of processing parameters in the cocoon drier 'Elektronika TKSh-50' on the technological properties of cocoons. "Sholk (silk)," #3, 21–23.

The foregoing shows that drying of silkworm pupae and cocoons by IR radiation generated by the ceramic compositions of the invention preserves the physiologically active compounds in the pupae. This broadens the scope of possible uses of extracts of pupae in fields such as biotechnology, food processing, drug manufacture, and fodder production. Moreover, the invention provides a simplicity of drying that may be employed in a wide range of possible drying apparatus with a high level of environmental safety.

TABLE 13

| ambient pH | 9.0 | 10.0 | 11.0 | 10.0 (without $CaCl_2$) |
|---|---|---|---|---|
| METHOD OF DRYING AND ACTIVITY | | | | |
| 1. Phospholipase activity after sublimation drying* | 17.3 | 32.5 | 17.5 | 35.0 |
| 2. Phospholipase activity after convective heat drying* | 5.3 | 11.2 | 4.8 | 13.1 |
| 3. Phospholipase activity after UHF drying* | 9.7 | 18.8 | 7.5 | 20.0 |

TABLE 13-continued

| ambient pH | 9.0 | 10.0 | 11.0 | 10.0 (without $CaCl_2$) |
|---|---|---|---|---|
| 4. Phospholipase activity after IR drying according to the invention* | 15.0 | 28.2 | 13.4 | 31.6 |

*Phospholipase activity is measured by potentiometric titration as given in G. H. De Haas et al., Biochem. et biophys. acta, 1968, 159, p. 118. Phospholipase activity is expressed in mmol/min × ml of 1% solution of the pupae sample.

TABLE 14

| Synthetic substrates of the proteases | 1.0% solution of a pupae sample in $H_2O$ | 0.1% enzyme solution in $H_2O$[2] | Protease Activity[1] | |
|---|---|---|---|---|
| | | | $UHF^3$ | IR |
| BAEE | 0.1 ml | — | 0.00 | 0.30[4] |
| BAEE | — | 0.1 ml of tr | 1.80 | 1.80[5] |
| BAEE | 0.01 ml | 0.1 ml of tr | 1.60 | 1.50[5] |
| BAEE | 0.05 ml | 0.1 ml of tr | 0.96 | 0.82[5] |
| BAEE | 0.1 ml | 0.1 ml of tr | 0.73 | 0.53[5] |

TABLE 14-continued

| Synthetic substrates of the proteases | 1.0% solution of a pupae sample in $H_2O$ | 0.1% enzyme solution in $H_2O^2$ | Protease Activity[1] | |
|---|---|---|---|---|
| | | | UHF[3] | IR |
| BAEE | 0.3 ml | 0.1 ml of tr | 0.00 | 0.00[5] |
| ATEE | 0.1 ml | — | 0.00 | 0.54[6] |
| ATEE | — | 0.1 ml of ctr | 3.4 | 3.40[7] |
| ATEE | 0.1 ml | 0.1 ml of ctr | 0.7 | 0.56[7] |
| ATEE | 0.3 ml | 0.1 ml of ctr | 0.36 | 0.00[7] |

[1]Activity of the proteases is measured by potentiometric titration in a automatic titrimeter produced by "Radiometer," Denmark. Activity is expressed in relative values, i.e., the slope (tan) of the kinetic curves under constant conditions of testing. See N. R. Dzhanbaeva et al., "Investigation of Menolytical Elements of Cotton Seeds," Chemistry of Natural Compounds N2, pp. 222–228, 1972.
[2]Designations: tr — trypsin, ctr — chymotrypsin
[3]B. Ys. Khaimov, A. Abdullayev, G. I. Arkhipova, M. Ya. Bakirov. "A study of the properties of cocoons dried in an UHF field in cocoon driers 'Elektronika TKSh-50'." Report 3. Effect of processing parameters in the cocoon drier 'Elektronika TKSh-50' on the technological properties of cocoons. "Sbolk (silk)," #3, 21–23.(1985)
[4]Comparisons of Trypsin-like activity
[5]Comparisons of Inhibitor of Trypsin activity
[6]Comparisons of Chymotrypsin-like activity
[7]Comparisons of Inhibitor of Chymotrypsin activity

Preservation of Bio-materials

As indicated, the invention generally can be employed in biotechnology applications. More specifically, the invention can be employed in methods of concentrating, drying, and sterilizing biologic objects. The invention also may be employed in agriculture, light industrial processes such as textiles, food, microbiologic, pharmaceutical and fodder industry, as well as in treating and sterilizing waste products and sewage.

Various methods for concentrating liquids, extracts, and homogenates of biological tissues by filtering, sedimentation, chromatography, electrophoresis, and membrane technology is known. See, G. E. Bagley, D. F. Oilis, Biochemical Engineering Fundamentals (Russ) 1989, Moskwa, MIR, V2, P255–345. All these methods have limitations in that concentration of a biological material does not go to completion. Also, due to residual water content, the final product can be stored only for a limited time.

The known method of sublimation provides products with little or no residual water. However, sublimation entails deep freezing which can disintegrate the cellular structure of the biomaterial to be dried. Sublimation also is too expensive for drying of inexpensive raw materials products on an industrial scale. Sublimation also takes a relatively long time, and must be performed in a batch-wise manner.

UHF-drying with vacuuming or forced ventilation also has been used for concentrating and drying of bioproducts. This method also is expensive and is not used in industry. Moreover, products prepared by this method lose a large amount of essential oils and some of the physiologically active substance is denatured.

The present invention, however, surprisingly enables concentrating, drying and simultaneously sterilizing the biological body without destroying the physiological activity of biologically active substances such as enzymes, vitamins, hormones, easily oxidized compounds, essential oils, and the like.

In accordance with the invention, a biological body or a portion thereof, in a form such as liquid, disintegrated body, or paste is exposed to infrared (IR) in a range of wavelengths of 2 to 9 mcm radiation generated by a bi-layer ceramic transforming screen of compositions C and B. In the bi-layer screen, composition C is the inner layer which is directly heated a thermo-electric element. Composition B forms the outer layer of the bi-layer screen nearest the material being treated. The screen is heated to 180° C. to 300° C. to generate IR radiation. The range of wavelengths generated by the bi-layer ceramic screen provides maximum absorption of IR radiation by the water in the biomaterial and a minimum absorption of IR radiation by the physiologically active and other organic compounds of the biomaterial.

Moreover, since the wavelength of IR radiation can be selected to excite and evaporate only the water molecules in the biological material, the overall effect of drying is much more energy efficient than in the prior art where part of the energy is wasted on heating the body itself which tends to destroy the physiological activity of the biomaterial.

Example 15

Whole biological objects or their parts, as well as compositions made from agricultural products, are treated by IR radiation generated as described above by the bi-layer ceramic screen formed of formulations C and B. These objects include cabbage (shreds 10–50 mm long); red carrot (chips); mulberry leaves (*Worus alba*); whole plants of horseradish (Armoracia); melissa and basil. Green parts of these materials are cut into pieces measuring 10–50 mm long and formed into a pasty artificial food for silkworms. The food is provided in the form of granules, and shreds of these materials are deposited onto plastic sheets. Also treated with IR radiation are caterpillars, pupae, and cocoons of the silkworm (*Bombyx mori*), a pig pancreas (minced), yeast, and phospholipase D immobilized on silica gel—see SH. R. Madjarov, N. Sadieova, "Phospholipase D from Soybean—the preparation for Hydrolysis and Synthesis of phospholipid (Russ) Catalysis and Catalytical Process Chenpharm productions," All Union Conference 1989. FAN Tashkent V2. All the above-mentioned samples are placed on woven-wire trays. Pasty samples (i.e., the artificial food for the silkworm and immobilized phospholipase D) are dried in Petri plates or on thin plastic sheets. Drying with IR radiation is done in a drier with forced ventilation so that the temperature is maintained at 50° C.

Example 16

Various liquid biological materials are concentrated and, or dried as in Example 15. These materials include the hemolymph of healthy silkworm caterpillars, and of caterpillars suffering from hepatic of the silkworm; an unseparated culture liquid of the fungus *Trichcoderma lignorum* (—See G. Tashpulatov, K. H. Gelatova, T. Abdullae, M. Mipsaraasikova, "Trichoderma Liquoram 19 Cellutase (Russ) in Cellutases of the Microorganisms," Nayka, Moskwa, 1981, p114–128) containing the cellulolytic enzyme complex with the fungus itself; a 0.5% solution in $H_2O$ of the basic protease *B. subtills* from the Ladyzhino biochemistry plant; a 0.1% solution in $H_2O$ of cattle pancreas-derived trypsin from "Spofe" (Czechoslovakia); and sewage of Tashkent silk-unravelling plant. Liquid samples (concentration 0.1–1% in $H_2O$) of these materials are placed into dialysis tubes measuring 6 mm in diameter and 350 mm long, manufactured by "Serva" (Germany). The lower end of the tubes is plugged, and into the upper end is inserted a feeding funnel containing a solution of the biomaterial. A thermometer is placed in the center of a control dialysis tube. The tubes are exposed to IR radiation in the desired wavelength (2 to 9 mcm) while artificially ventilating to maintain a temperature of the airflow of 40°–50° C. The temperature inside the tube varied from 18° to 22° C. and the rate of concentrating is 1 ml per 8 min. When the biomaterials are in the form of liquids, the liquid can be concentrated to a desired degree so that the process can be performed continuously by pumping the liquids through the dialysis and hollow tubes and returning them into the tank.

Figure 9A:
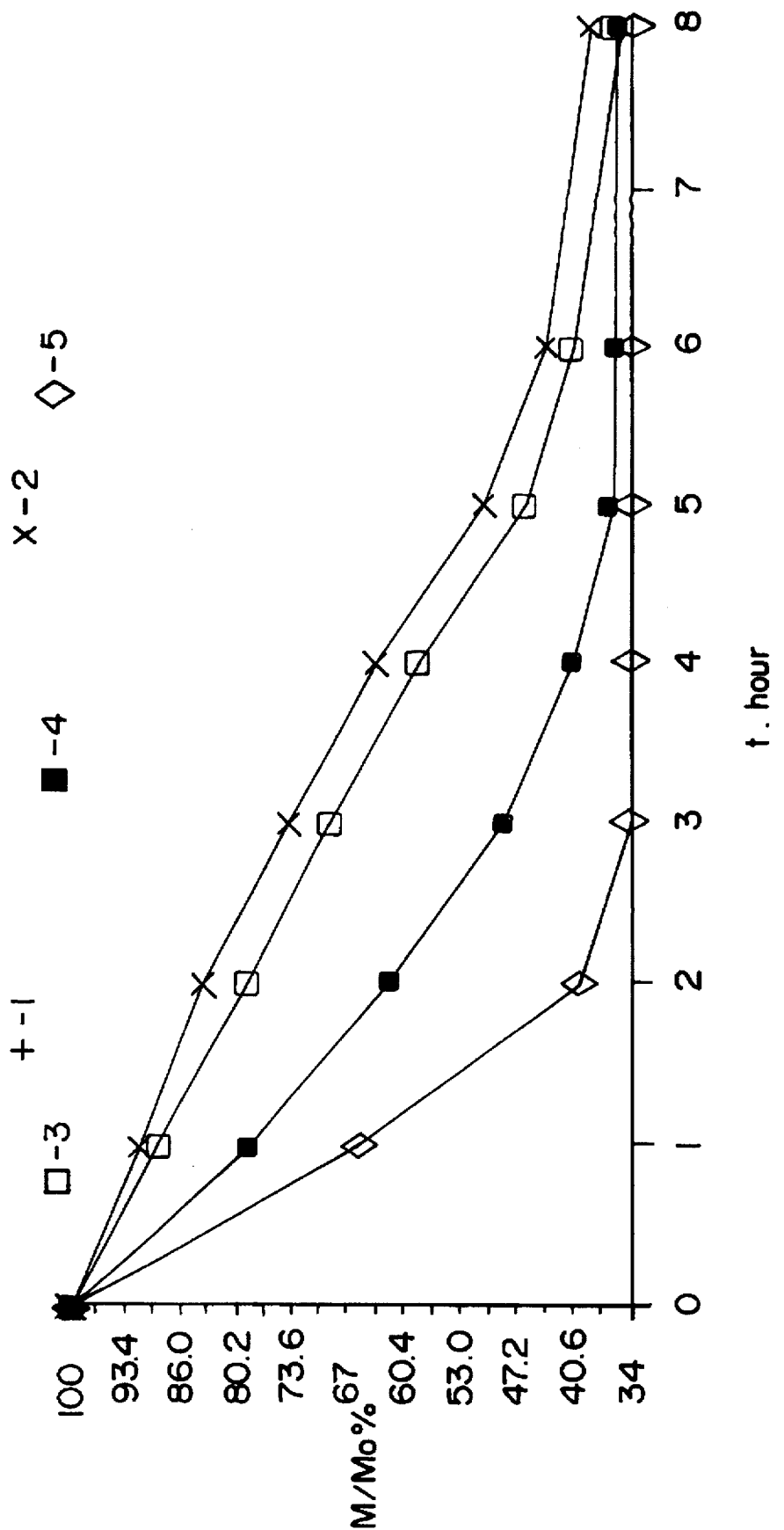

The kinetics of drying of the materials is measured on a pasty artificial food for silkworm prepared by blending a dry feeding mix containing mulberry leaf powder, soybean flour and, as a partial substitution for the soybean flour, a flour containing cotton seeds, silkworm pupae, sericin powder, chlorella powder, as well as B-group vitamins with water in a ratio of 1:2. (See SH. R. Madjarov, N. M. Khalmoviraev, U. N. Nosirilner, N. K. Ababakirov et al. Nitrions for silkworms breeding/Soviet patent N1475568, Mar. 1, 1989). The pasty food is prepared in various forms such as granules and shreds of various size. The food is deposited onto thin plastic sheets. As can be seen from FIG. 9a, granules and shreds placed in a container (Petri plates) are dried in 8 hours. Granules and shreds of the pasty food deposited on the plastic sheets is dried in 5 hours. The granules (and shreds) dried most quickly when the thickness of a layer does not exceed 2.5 cm.

The nutritional value of the artificial food is judged by its effect on the aged increase in weight of the silkworm caterpillars. The activity of other biological substances of the food is judged from the fermentation activity of the food. Fermenting activity is used because decay due to fermentation, e.g., denaturation, begins at 30° Celsius.

The biological activities of ferments of biological substances such as the aforementioned artificial food are determined as follows: the proteolytical activity is measured by potentiometric titration with the aid of synthetic substrates of BAEE and ATEE. Cellulosolytical activity is determined by the spectrophotometrical method in accordance with secreting of color from colored substrate OC-31, See Lyalikov, *Physical and Chemical Methods of Analysis*, 4, 1978. Activity of phenoloxidiase is determined in accordance with oxidation of pyrocatechin by the well-known polarographic method; respiration of brains is determined in accordance with the rate of oxidation of glutamine by the polarographic method; the activity of phospholipase D is determined in accordance with the rate of hydrolysis of lecithin; the activity of phospholipase A2 is determined in accordance with the methods described in G. H. DeMaas, N. M. Postema, W. Neuweuhuizen, L. L. M. Van Deahen Biochem and Biophys, ACTA sets 1968 V158m P118–126.

In Table 15, data is presented on the weight gain of silkworm caterpillars (tetrahybrid-3) from artificial foods derived by the aforementioned methods. As a control, fresh leaves of mulberry are employed as a food. See USSR patent N1415568. In addition we tested the effects of the powder of leaves of mulberry, the powder or fat deleted pupae of the silkworm, and the powder of cericine from steaming apparatus is provided. Powders of pupae and cericine can be used as protein additions to the artificial food and can be added as a substitute for corresponding quantities of low-fat soy flour. Powder of leaves of mulberry, however, is employed in all diets because powder of these leaves plays a role as a food attractant and has the entire collection of flavoring and phagostimulating substances.

As seen from Table 15, the much more expensive sublimation method and the method of the invention give comparable results to those obtained with the control method which uses fresh leaves of mulberry. Artificial foods generated from microwave dried foods, however, generates a much lower weight gain. Also, powders of both low-fat pupae and cericine produced as by-products of silk production contain almost the same amino acids and other physiologically active substances as secreted by the pupae itself. These powders therefore are useful as biostimulators.

As regards analysis of properties of other biological materials by the above tests, we compare the activity of ferments with fresh (not dried) materials. For example, in homogenates of plant samples, the following activities of phospholipase D are obtained on materials dried by IR radiation (in units/g), as defined in SH. R. Madjarov, N. M. Khalmoviraev, U. N. Nosirillaev, N. K. Abubakirov et al., Nitrions for Silkworms Breeding/Soviet patent N1475568. The compositions of the samples and the activities of phospholipase D before/after drying of various plant samples are given below: cabbage 3.20/3.05; carrot 4.00/3.86; mulberry leaves 1.50/1.62; immobilized on silicogel phospholipase D+ from soy flour 42/38. Also, the activity of phospholipase A2 in (units/g) on various materials treated with IR radiation as above is provided: ground pig pancreas activated by endogen proteases (see G. H. DeMaas, N. M. Postema, W. Neuweuhuizen, L. L. M. Van Deahen Biochem, et Biophys, ACTA 1968 V158m P118–126) is 0.50/0.46; pupae of silkworm is 0.20/0.18. The activity(units/mg) of trypsin from the SOPFA Compound, (a Czechoslovakian Co.) in 0.1% solution in $H_2O$ on BAEE is 8.0/7.6; proteases B subtills is 0.72/0.70. In cultured liquid *Trichoderma liquorium* the general cellulose activity (in units of $D_{490}$/hour mg)is 0.05/0.05. For the phenoloxidase activity (in units tan $\propto$/mg) we obtained for hemolymph of silkworm 0.30/0.25; for caterpillar: 0.09/0.085; for pupae: 0.11/0.40. For respiration of barre, measured (in Tan$\propto$/ml of 5% suspension) we obtained:37/32.

TABLE 15

| Drying Method and diet ingredients | Average Mass (grams) of Caterpillars in age groups | | | |
|---|---|---|---|---|
| | 2 | 3 | 4 | 5 |
| SUBLIMATION | | | | |
| 1. powder of mulberry leaves | 0.0205 | 0.089 | 0.280 | 0.72 |
| 2. powder of low-fat pupae 5%* | 0.0190 | 0.090 | 0.282 | 0.78 |
| 3. powder of cericine from steaming waters of silk production 2%* | 0.0202 | 0.087 | 0.273 | 0.75 |
| 4. control-the standard food (fresh mulberry leaves) | 0.0195 | 0.083 | 0.265 | 0.73 |
| UHF | | | | |
| 1. powder of dried mulberry leaves | 0.0163 | 0.67 | 0.205 | 0.58 |
| 2. powder of low-fat pupae 5%* | 0.0158 | 0.59 | 0.196 | 0.53 |
| IR ACCORDING TO INVENTION | | | | |
| 1. powder of dried mulberry leaves | 0.0192 | 0.085 | 0.273 | 0.73 |
| 2. powder of low-fat pupae 5%* | 0.0195 | 0.087 | 0.276 | 0.72 |
| 3. powder of cericine 2%* | 0.0197 | 0.020 | 0.270 | 0.70 |
| 4. control-the standard food (fresh mulberry leaves) | 0.0190 | 0.085 | 0.260 | 0.68 |

*Added instead of equivalent quantity (w/w) of low-fat soy flour.

From the foregoing data on fermentation, we surprisingly have observed almost total preservation of properties of biological substances during drying in accordance with the invention. Almost total preservation of properties of biological substances also is obtained for concentrated and dried biological liquids during treatment of liquid waste products and sewage.

We also have observed the additional benefit that the IR radiation drying process of the invention simultaneously sterilizes the food. This enables the food to be stored for longer periods without decay. For instance, artificial food dried by the method of the invention, after absorption of distilled water, is more stable to the action of microbes present in the environment. Stability of artificial food produced from material dried in accordance with the invention, when stored at 15 degrees celsius in hermetic packages, typically is 15–70 days. Dried food can be stored two times longer than food dried by conventional convective heat drying at 120° C. for 4–8 hours.

Organoleptic analysis of foodstuffs such as powder of horseradish, melissa and basil dried by the method of the invention shows almost total preservation of aromatic properties. This is especially seen for melissa which quickly looses its aromatic substances during the methods of drying of the prior art.

From the foregoing, the advantages of the method of concentration and drying of biological objects in accordance comparison with the invention include high efficacy of concentration and drying accompanied by sterilization; simplicity of the process; low consumption of energy; preservation of properties of physiologically active substances without loss of the biological substances and ether oils; and compatibility of the invention with existing biotechnological methods.

Drying of Plastic Materials

The invention also may advantageously be employed to dry plastic materials. A method of drying of plastic materials is known in which the plastic material is placed into an oven with a temperature of 120 degrees Celsius until a total loss of water is achieved. The process, however, usually takes more than 12 hours.

It is also known that drying can be accelerated and the quality of the dried plastic product can be improved by treating the material by IR radiation produced by transforming screen from mullite. See Authorized diploma USSR N366833 MKU 014 25/00 A0c1c 1/00-analog. The drawback of this method, however, is poor efficiency of drying.

In accordance with the invention, however, improved drying efficiency can be achieved if mullite with an addition of 0.5–4.0 wt. % of formulation C is employed as the transforming screen. Alternatively, a transforming screen formed of 1% Formulation A and 99% mullite can be employed. Heaters covered by ceramic transforming screens of formulation C also can be used.

To illustrate drying of plastic materials in accordance with the invention, polyamide is placed into a drying volume (oven) and treated by IR radiation formed by directing energy of a thermal source onto one ceramic transforming screen. Thermal Halogen lamps, or spiral wire heating elements placed into ceramic, glass, quartz-glass and metal tubes may be used to heat the ceramic screen to a temperature sufficient to generate IR radiation. The drying process continues until loss of the mass of treated object stops.

Example 15

For a comparative test, we employ a device having conventional thermoelectric nichrome radiators displaced at the bottom side of a net formed of stainless steel. The steel net is 200 mm from the radiators. The product to be dried is placed on the net.

We performed comparative tests comparing the effects of heating by nichrome wire in quartz glass tube covered by layer of mullite as disclosed above heated to 300° C., spiral nichrome wire placed into quartz glass tube covered by the aforementioned formulation B heated to 300° C., and spiral nichrome wire placed into quartz glass tube covered by the aforementioned composition C heated to 300° C. Results of these tests are shown in FIG. 12.

Figure 12:
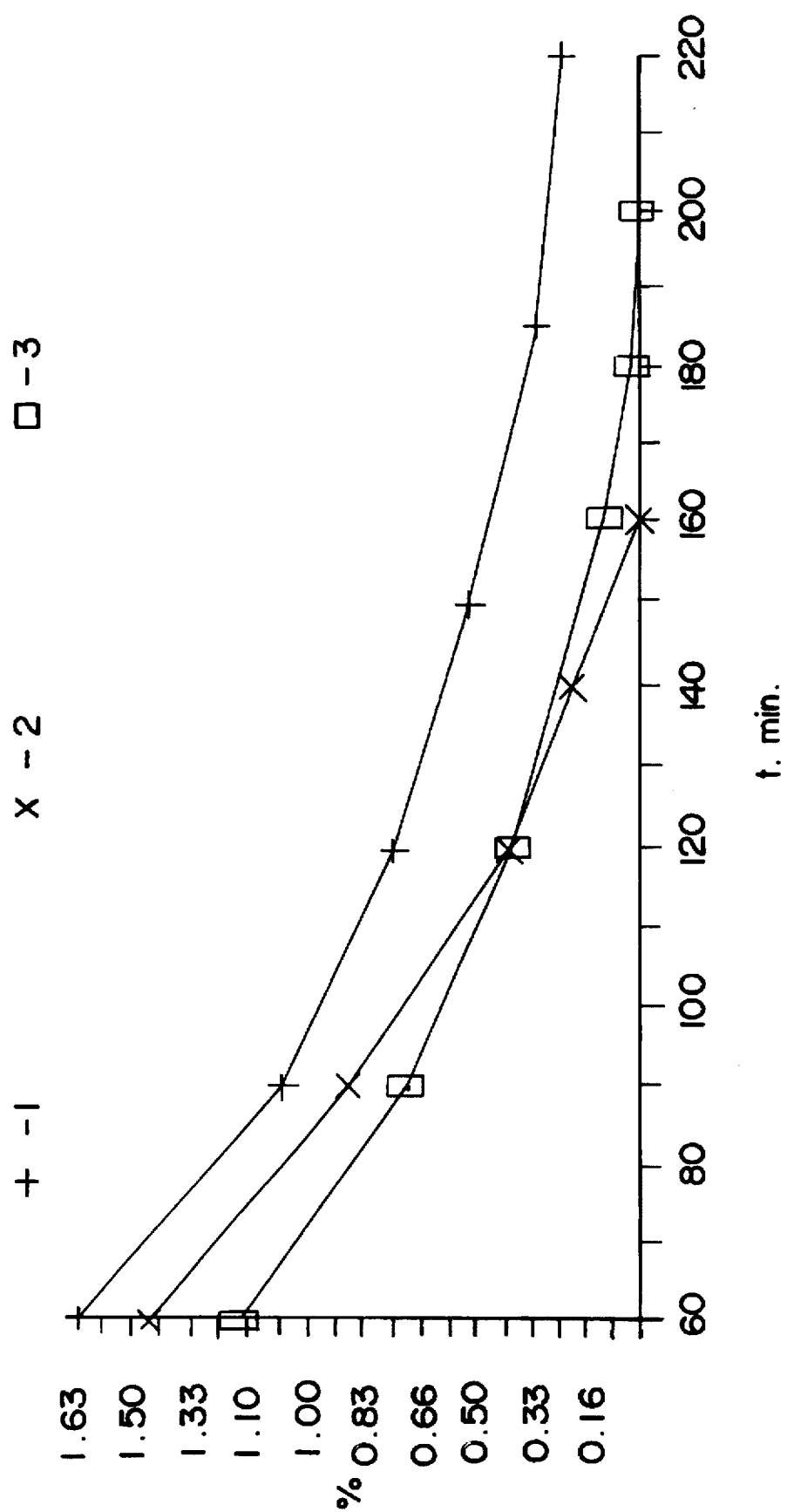
FIG. 12 shows the rate of drying of plastics materials by IR radiation.

As shown in FIG. 12, the maximal rate of drying is provided by transforming layer of formulation C, although at the beginning stage formulation B provides a higher rate of drying. Use of formulation C as transforming layer provides total drying during 160 minutes; composition B provides total drying during 200 minutes. The composition of mullite did not provide total drying.

Preservation of Foodstuffs

The invention also may be employed to preserve food stuffs. A method is known in the art for preserving food by placing the food into a hermetic chamber filled by an ozone-Aeron mixture of gases while the chamber is moved in a constant magnetic field. The drawbacks of this method are complexity of the treatment and short time of preservation since this method does not sterilize the treated fruits. Treatment of fruits by IR radiation in accordance with the invention, however, provides the benefits of more effective storage and preservation.

These benefits are achieved by treating foodstuffs such as fruits with visible radiation in the interval of 730–750 mm, and treating the samples with IR radiation generated by a ceramic transforming screen. As is known in the art, wavelengths in the interval of 730–750 nm can be generated by devices such as lasers, neon lamps, and the like.

Treatment with visible radiation of 730–750 mm and treatment with IR radiation slows degradation of fruits that preserves the main nutritious substances for surprisingly longer periods. Thermoelectric heaters and/or halogen lamps covered by a layer of the ceramic transforming screen is employed to generate IR radiation.

Example 16

Potatoes are treated with visible radiation of 750 nm for 1 min. at 100 W/m$^2$ after which they are treated by IR radiation generated by IR radiation generated a ceramic transforming screen of Formulation A heated to 200°–800° C. The IR radiation has an intensity of 2–6 KW/m$^2$ and is applied for one minute. Observations during a period of 6 months following treatment indicate that the potatoes are not damaged, did not sprout, and retained all the original nutritious properties. The control samples (untreated by IR radiation) sprouted after 2 months, and a portion of them (about 50%) are rotting.

Example 17

All operations are done as in Example 16 with the exception that carrots are treated. Observations made during 6 months after treatment that the carrots are not damaged, have not sprouted and retained all the original nutritious properties. The control (untreated) with IR radiation samples, however, are grown after 2 months and part of them (30%) are rotting.

Example 18

All operations are done as in Example 16 and 17 but onions are treated. Observations made during 6 months after treatment show that the onions are not damaged, did not sprout, and retained all the nutritious properties. Control (untreated by IR radiation) samples sprouted after 3 months and part of them (20%) are rotting.

Preservation of Plant Seeds

In addition to the foregoing, the method of the invention can be employed to treat seeds before planting. Treatment of seeds by concentrated solar radiation before planting is known. See Abstracts of reports to the 6th All Union Conference of Photoenergetics of Plants. pp. 168–169. Lvov, 1980. Microorganisms responsible for decay of the seeds, however, are not completely killed by the solar radiation.

Treatment in accordance with the invention, moreover, provides increased stability of the seeds against disease. The invention also stimulates the seeds for better growth to increase yield. These surprising advantages can be achieved by modifying the known method of treating seeds with visible radiation in the range of 630–680 nm and intensities of 0.05–140 w/cm$^2$ during 1–200 sec. to include treatment with IR radiation generated by ceramic screens. The wavelengths and intensities of visible radiation, as is known in the art, can be produced by laser, neon lamps, filters, and the like.

Ceramic compositions employed as transforming screens to generate the IR radiation are formed of formulation A. The ceramic composition is heated by a halogen lamp at 2–6 KW/M$^2$ for one minute to generate IR radiation to treat the seeds. Treatment of the seeds is performed by placing the seeds onto trays and treating them with visible radiation in the range of 630–680 nm at an intensity of 0.05–140 w/cm$^2$ for 1–200 sec. The seeds then are treated with IR radiation generated from the ceramic transforming screen.

Example 19

Seeds of cotton are exposed to visible radiation with wavelengths of 660 nm at an intensity of 0.05 W/cm$^2$ during 200 sec. At the same time they are treated by IR radiation with an intensity of 2–6 KW/m$^2$ for 30–90 seconds generated by ceramic formulation A heated to 300–800 C. Treated seeds are grown and the percentage of grown seeds is found to be 99.8. Seeds not treated with IR radiation yielded only 96% growth. Observations show that grown plants derived from seeds treated in accordance with this example are stable to diseases such as black root rot and rizoktonioz. In contrast, 6% of the seeds which were not treated with IR as in the example yielded plants with black root rot and 4% of the seeds yielded plants with rizoktonioz.

Example 20

Seeds of tomato are exposed simultaneously to visible radiation with wavelengths of 630 nm at the density 140 w/cm2 for 1 sec., and to IR radiation generated by ceramic transforming screen of composition A heated to 300°–800° C. Treated seeds are grown and the percentage of grown seeds is found to be 99.3%; for seeds treated only to the visible radiation, we have 93% growth. Diseases for seeds and grown plants are not observed with seeds treated by IR. In contrast, 32% of the plants which were not treated by IR as in the example became diseased.

Example 21

Seeds of pepper are exposed simultaneously to radiation with visible radiation of 680 nm at an intensity of 40 w/cm2 during 3 sec., and to IR radiation generated by ceramic composition A healed to 300°–800° C. Seeds are grown and the percentage of grown seeds is found to be 99.4%. In comparison, the percentage of grown seeds produced by treating the seeds with visible radiation and IR radiation generated by a mullite screen heated to is only 89%. Diseases are not observed in plants grown from seeds treated by IR radiation generated by formulation A in accordance with this example. In contrast, 23% of plants grown from seeds treated with IR generated from the mullite screen became diseased. The method of these examples show high effectiveness, steadiness and simplicity of the treatment method disclosed herein.

Baking and Cooking of Foodstuffs

The IR radiation generated by the ceramic material of the invention also may be employed to roast and bake food products. The drawbacks of the usual methods of roasting and baking are the low quality of the final product since a considerable amount of moisture is evaporated. The known methods also have a high consumption of energy, and take a long period of time. Also, roasting of potato chips has drawbacks related with extensive use of oil. Because frying of potato chips in oil is performed at high temperatures, carcinogens and other substances can be produced. The use of IR radiation produced by the invention, however, allows one to eliminate these drawbacks.

Roasting and baking processes which employ IR radiation differ from the previously described methods where IR radiation is used in drying. First of all, the intensity of IR radiation generated per unit area of ceramic transforming surface is at least 4 times higher than that employed for drying. Secondly, roasting and baking is performed in a closed volume so that moisture produced from the food is not lost from the volume. Baking and cooking of foodstuffs by IR radiation employs ceramic screens of formulation C. These screens emit IR radiation in the far infrared region. The screens are heated to 600° C. to 800° C. to generate IR radiation. Radiation in this part of the IR spectrum has strong penetrating abilities.

Example 22

One kg. of bread dough is placed onto a tray and then put into a closed oven with IR radiators of formulation C. The IR radiators are made by coating a thermoelectric heater with ceramics of composition C. The thermoelectric heater is energized to raise the temperature of composition C to a temperature of 700° C. to generate IR radiation. The process is continued for 4–6 minutes.

The loss of mass of the product because of evaporation of moisture is (5.5–6%). For the usual baking oven with conventional thermoelectric heaters, loss of moisture is 28%. Energy consumption for baking 1 kg of bread is 0.06 KWH, whereas the conventional method requires 0.23 KWH. The time of baking is 6–10 times less than conventional convective heating.

Example 23

One kg. of beef cut into 3.5 cm cubes is put on a stick and placed into an oven with IR radiators made by depositing a layer of composition C onto a thermoelectric heater as in Example 22. The radiators are heated as in Example 22, and the process of roasting is continued for 4–6 minutes. The loss of mass of the beef due to evaporation of moisture is 2.5–3%. For conventional thermoelectric heaters, the loss of mass is 26–30%. The energy consumption for roasting of 1 kg of beef is 0.07 KWH, whereas the energy consumption required by conventional thermoelectric heaters is 0.32 KWH. The time for roasting by the method of the invention, moreover, is 4–7 times less. Also the appearance of both the bread and the meat prepared by the method of the invention is much better; this is true for other organoleptic features of the final product as well.

Example 24

One kg. of potato slices with thickness of 5 mm suitable for potato chips are put on a tray and placed into an oven with IR radiators as described in Example 22. The radiators are heated as in Example 22. The process of roasting the chips is continued for 3–5 minutes. The mass loss due to moisture evaporation is 5–8%. Practically the same results are obtained for potatoes prepared in the form of french fries.

The method can be employed without use of oil. The method enables preservation of the food's nutritional properties as well as taste, appearance and flavor.

Accelerated Wine Aging

IR radiation generated in accordance with the invention also may be employed to accelerate fermentation and aging of wines. This enables the desired taste to be achieved in a much shorter time than with conventional aging by storage.

Accelerated ageing of wine can be achieved by employing thermo electric radiators which have a transforming screen of bi-layer ceramic coating which are heated to 180°–300° C. Typically, the infrared radiation generated by the bi-layer ceramic screen is applied for two minutes per two liters of wine so that the temperature of the wine does not exceed 55 C. The bilayer screen is formed of formulations C and B, where C is the inner layer and B is the outer layer nearest the wine.

Two days after exposure to IR radiation as described above, the characteristics of wine aged for 2 years of age storage of wine is judged from organoleptic tests. Organoleptic tests of the wine indicate yellowing of wine, improvement of tint of color (for green wines), a decrease of viscosity(for viscid wines), and improvement of taste and flavor. In addition to these benefits, treatment with IR radiation according to the invention also significantly decreases foetals of diseases. Pathogen factors also are destroyed and excesses of iron containing compounds and substances are changed into sediment.

Water Desalination

As a further use of the method of generating IR radiation according to the invention, the invention can be employed to rapidly and effectively desalinize water. Conventional methods of desalination of water, such as by distillation, has a number of disadvantages. These disadvantages include high energy consumption and long time periods. The method of desalination by using IR radiation generated in accordance with the invention, however, avoids these disadvantages.

Desalination by IR radiation is accomplished by providing a transforming screen of a ceramic of formulation of either A or C on the surface of a thermoelectric wire heating element. Water is placed under the coated heating elements and exposed to IR radiation generated by heating the transforming ceramic screen to a temperature of 500–800 C.

Figure 13:
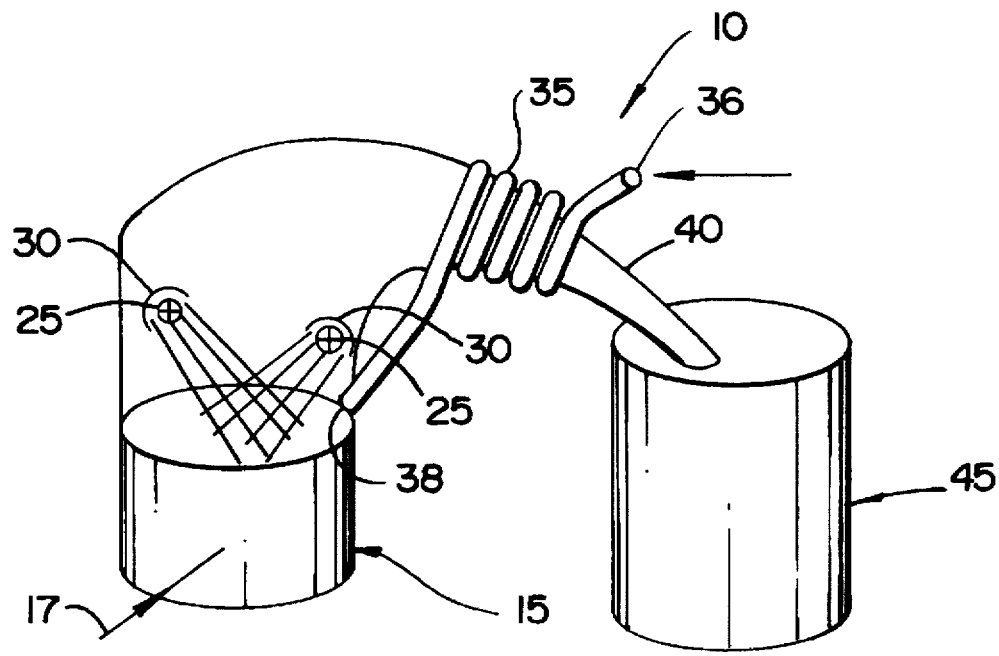
FIG. 13 is an illustration of an apparatus for desalinizing water by IR radiation.

A device suitable for employing the IR radiation generated in accordance with the invention to desalinate water is shown in FIG. 13. Device 10 includes an enclosed tank 15 for receiving water. The water is heated by IR radiation generated by IR radiators 25 formed of a thermoelectric heating element bearing a ceramic transforming screen. Reflectors 30 of, for example, a heat resistant reflective metal such as aluminum, are provided above radiators 25 to reflect IR radiation downwardly onto the surface of water 17 in tank 15. A combination water supply conduit-heat exchanger 35 is provided on outlet conduit 40. Helical, conduit-heat exchanger 35 has inlet 36 for receiving water to be desalinated from a source(not shown), and outlet 38 for supplying water to tank 15.

In operation, water to be desalinized is supplied through conduit-heat exchanger 35 to tank 15. The rate of water supplied to tank 15 is controlled to approximately equal the amount of water vapor generated by the IR radiation. This enables the level of water in tank 15 to remain nearly constant. Water vapor generated rises and passes through outlet conduit 40 which bears conduit-heat exchanger 35 thereon. Flow of incoming supply water through heat exchanger 35 to tank 15 cools conduit 40 to thereby condense water vapor generated in tank 15 provide desalinated water to receiving tank 45.

As mentioned, incoming supply water flowing through exchanger 35 to tank 15 cools conduit 40 to condense the water vapor. Simultaneously, the incoming supply water is heated by the water vapor to provide preheated water to tank 15. Consequently, high energy savings is achieved in-part because the water to be desalinized is preheated. Also, increased energy efficiency is achieved because the JR radiation vaporizes the surface of the water 17 without heating the bulk of the water as required by conventional prior art methods.

Accelerated Drying of Painted Surfaces

Drying by IR radiation generated by ceramic materials in accordance with the invention also has utility in paint coating applications such as the automotive industry. In particular, drying by IR radiation in accordance with the invention has particular application to drying of enamel and lacquer paints employed as automotive finishes to provide finishes of surprisingly improved lustre.

It is known in the art that use of convective heat and radiation from halogen lamps to dry paints such as automotive finishes takes an extended period of time and tends to not produce a high quality finish. These deficiencies tend to result from the fact that drying by these methods form a dry surface layer which prevents removal of solvent from the inner layers of the paint finish. Use of IR radiation in accordance with the invention, however, penetrates the paint to heat the underlying base(usually metal) to avoid formation of a dried surface layer to thereby more rapidly dry the paint. Moreover, drying with IR radiation yields improved adhesion of the coating to the base than the conventional drying methods of the art. As a result, the paint finish is characterized by improved reflectance and lustre.

As an illustration, it is known that drying of automotive enamel on metal by halogen lamps which generate a temperature of 80° C. on the surface of the enamel requires two hours. In surprising contrast, drying of the same enamel finish by IR radiation generated by a bilayer transforming ceramic screen of formulations C and B described above, when heated to 600° C. such as by a halogen lamp, only requires 2 minutes. Not only is the drying time greatly reduced with a resulting energy savings, but also the quality of the finish is very high since adhesion of the paint to the base is at least two times more than that of the produced by conventional drying with halogen lamps. The magnitude of adhesion of the paint to the underlying metal substrate is measured in the following manner: two metal disks, one of which is painted and the second of which is covered with glue, are pushed against each other under a constant pressure. The disk covered with glue is rotated relative to the painted disk while maintaining the applied pressure. The force required to rotate the disk coated with glue to destroy the painted surface of the other disk is measured. Organoleptic results, moreover, showed that the reflectance and uniformity of the finished surface is superior than that obtainable from the art.

We claim:

1. A composition comprising mullite and between about 0.5 and 4 wt. % of a ceramic composition consisting essentially of 44.7% $Cr_2O_3$, 28 wt. % $Fe_2O_3$, 17 wt. % $SiO_2$, 5.5% CaO, 2.5 wt. % $Al_2O_3$, 2 wt. % MgO, and 0.3 wt. % CuO.

2. A composition comprising mullite and between about 0.5 and 4 weight percent of a ceramic composition comprising 44.7% $Cr_2O_3$, 28 wt. % $Fe_2O_3$, 17 wt. % $SiO_2$, 5.5% CaO, 2.5 wt. % $Al_2O_3$, 2 wt. % MgO, and 0.3 wt. % CuO.

* * * * *